United States Patent
Birchak et al.

(10) Patent No.: US 6,412,354 B1
(45) Date of Patent: Jul. 2, 2002

(54) VIBRATIONAL FORCED MODE FLUID PROPERTY MONITOR AND METHOD

(75) Inventors: James R. Birchak, Spring; Mark A. Proett, Missouri City; Thomas E. Ritter, Katy; Vimal V. Shah, Houston, all of TX (US); Curtis M. Vickery, Duncan, OK (US)

(73) Assignee: Halliburton Energy Services, Inc., Duncan, OK (US)

( * ) Notice: Subject to any disclaimer, the term of this patent is extended or adjusted under 35 U.S.C. 154(b) by 0 days.

(21) Appl. No.: 09/464,728

(22) Filed: Dec. 16, 1999

(51) Int. Cl.[7] .............................. G01F 1/84; G01F 1/66
(52) U.S. Cl. .............................. 73/861.356; 73/861.27
(58) Field of Search .................... 73/861.351, 861.354, 73/861.356, 861.357, 861.27, 861.28, 861.29, 861.31, 861.18

(56) References Cited

U.S. PATENT DOCUMENTS

| | | | |
|---|---|---|---|
| 3,903,731 A | 9/1975 | Sieben .......................... 73/54 |
| 3,965,308 A | 6/1976 | Scarpa ...................... 73/194 A |
| 4,164,865 A * | 8/1979 | Hall et al. ................. 73/194 A |
| 4,193,291 A | 3/1980 | Lynnworth ................... 73/32 A |
| 4,240,285 A | 12/1980 | Langdon .......................... 73/32 |
| 4,341,111 A | 7/1982 | Husar ......................... 73/64.1 |
| 4,420,983 A | 12/1983 | Langdon ..................... 7/861.18 |
| 4,513,625 A | 4/1985 | Campman et al. ....... 73/861.72 |
| 4,524,610 A | 6/1985 | Fitzgerald et al. ............. 73/54 |
| 4,566,181 A | 1/1986 | Matsusik et al. ......... 29/602 R |
| 4,571,693 A | 2/1986 | Birchak et al. ............. 364/509 |
| 4,612,814 A | 9/1986 | Campman ................. 73/861.72 |
| 4,628,725 A | 12/1986 | Gouilloud et al. ............. 73/19 |
| 4,698,792 A * | 10/1987 | Kurjian et al. ................ 367/31 |
| 4,949,583 A | 8/1990 | Lang et al. ............... 73/861.37 |
| 5,150,061 A | 9/1992 | Castel et al. ................ 324/640 |
| 5,321,991 A | 6/1994 | Kalotay ..................... 73/861.37 |
| 5,323,658 A | 6/1994 | Yao et al. ................. 73/861.37 |
| 5,497,665 A * | 3/1996 | Cage et al. ............. 73/861.356 |
| 5,571,952 A | 11/1996 | Kauzlarich ................. 73/54.24 |
| 5,616,868 A | 4/1997 | Hagenmeyer et al. . 73/861.357 |
| 5,705,754 A | 1/1998 | Keita et al. ............. 73/861.357 |
| 5,710,374 A | 1/1998 | Ross et al. .................. 73/54.24 |
| 5,736,653 A | 4/1998 | Drahm et al. .......... 73/861.356 |
| 5,741,953 A | 4/1998 | Birchak et al. .......... 73/152.16 |
| 5,796,001 A | 8/1998 | Greiff et al. ............. 73/504.16 |
| 5,796,010 A | 8/1998 | Kishiro ................... 73/861.357 |
| 5,804,741 A | 9/1998 | Freeman ................ 73/861.356 |
| 5,854,430 A | 12/1998 | Drahm et al. .......... 73/861.357 |
| 5,865,871 A | 2/1999 | Simundich .................... 73/861 |
| 5,900,534 A | 5/1999 | Miller et al. ............... 73/24.05 |
| 5,969,265 A * | 10/1999 | VanCleve et al. ....... 73/861.355 |
| 6,065,350 A * | 5/2000 | Hill et al. ................. 73/861.27 |

FOREIGN PATENT DOCUMENTS

| WO | WO 99/04254 | 1/1999 |
|---|---|---|

* cited by examiner

*Primary Examiner*—Helen Kwok
(74) *Attorney, Agent, or Firm*—John W. Wustenberg; Craig W. Roddy; E. Harrison Gilbert, III

(57) ABSTRACT

A fluid property monitor includes a transducer assembly to impart multiple frequency energy to a conduit in one or more modes and to receive resonant frequency energy from the conduit. The resonant frequency energy is responsive to the imparted energy, the conduit and a fluid in the conduit. The fluid property monitor can also be defined as including: a frequency signal generator connected to cause multiple frequency energy to be transferred to a conduit having a fluid to be monitored; and a spectral analysis signal processor connected to receive and process electrical signals generated in response to vibrations propagated through the conduit and the fluid in the conduit in response to transferred multiple frequency energy. Particular implementations can be adapted as a densitometer, a coherent flow detector, and other particular fluid parameter detectors. A method of monitoring a fluid includes: imparting multiple frequency vibration-inducing energy to a conduit and fluid system; and sensing a plurality of frequency signals from the conduit and fluid system responsive to at least part of the imparted multiple frequency vibration-inducing energy. This method can also include determining at least one characteristic of the conduit and fluid system in response to the sensed plurality of frequency signals.

27 Claims, 17 Drawing Sheets

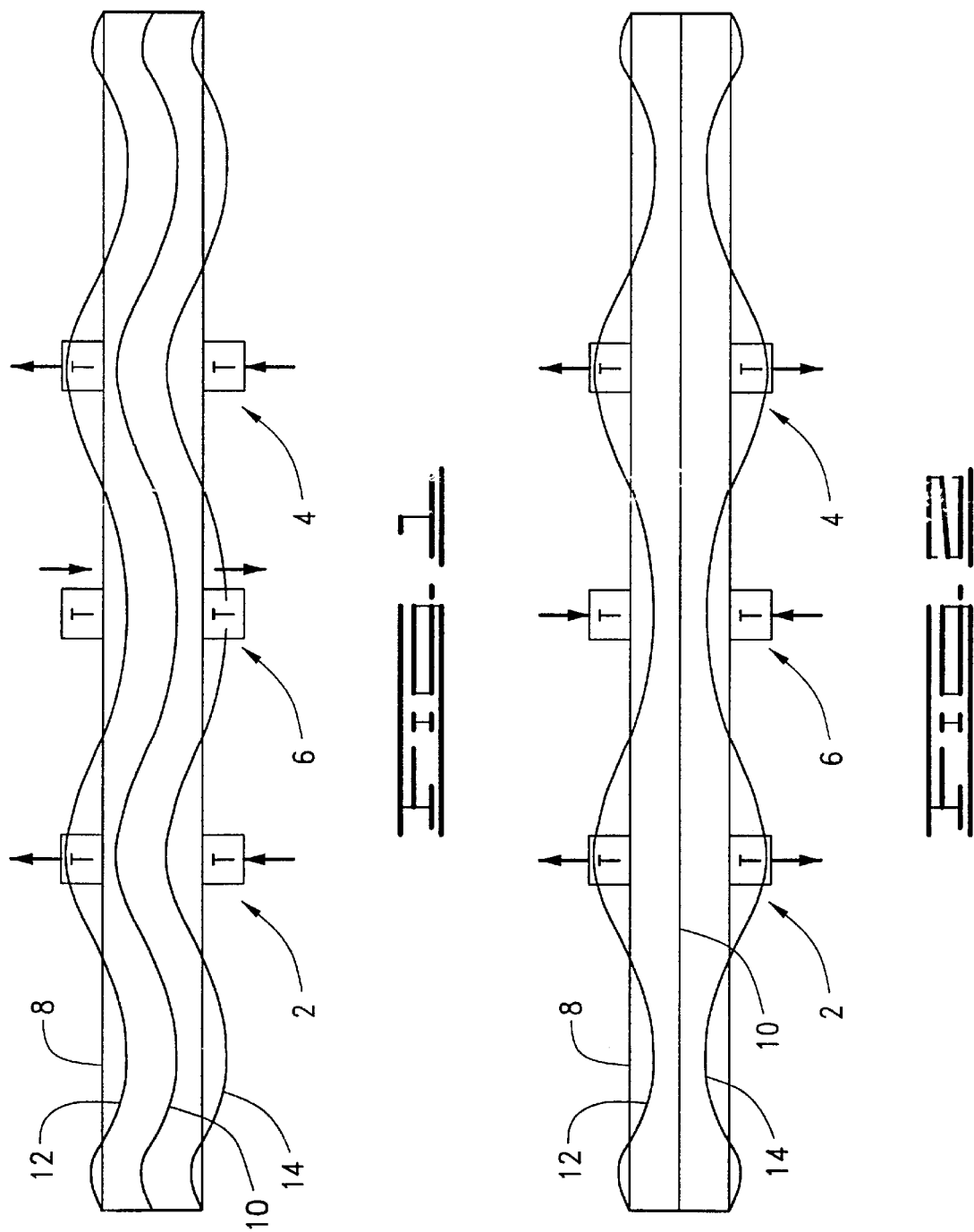

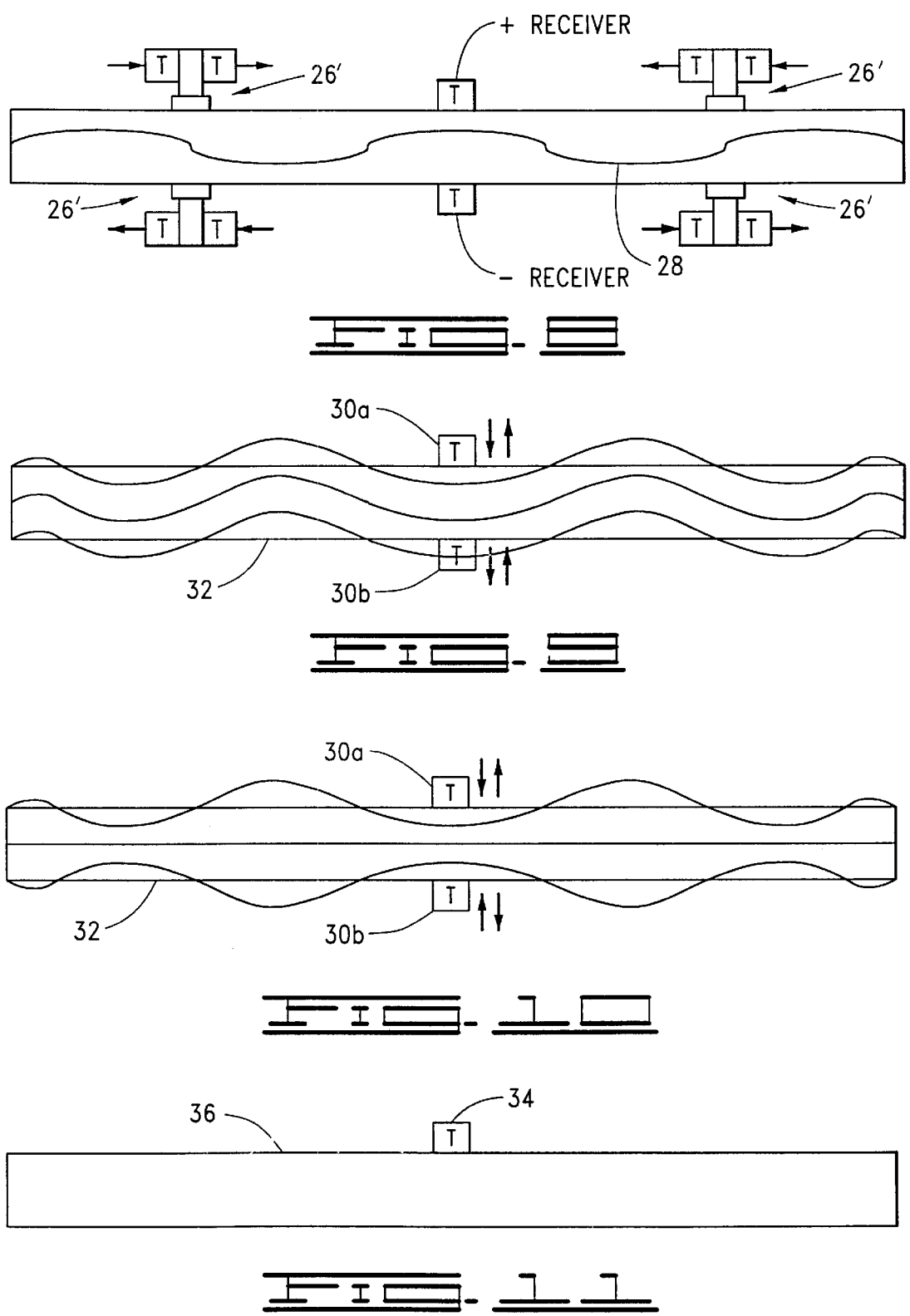

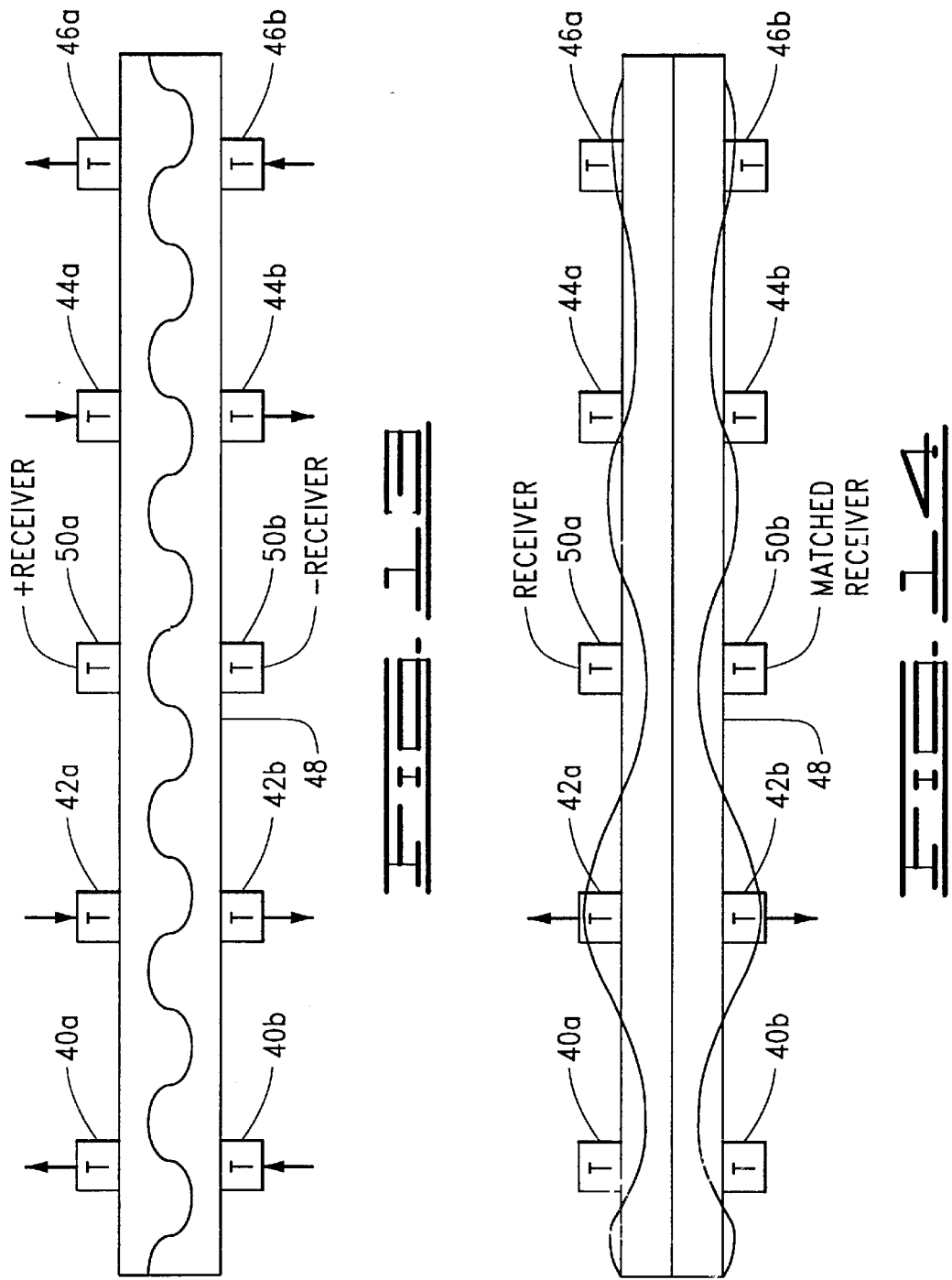

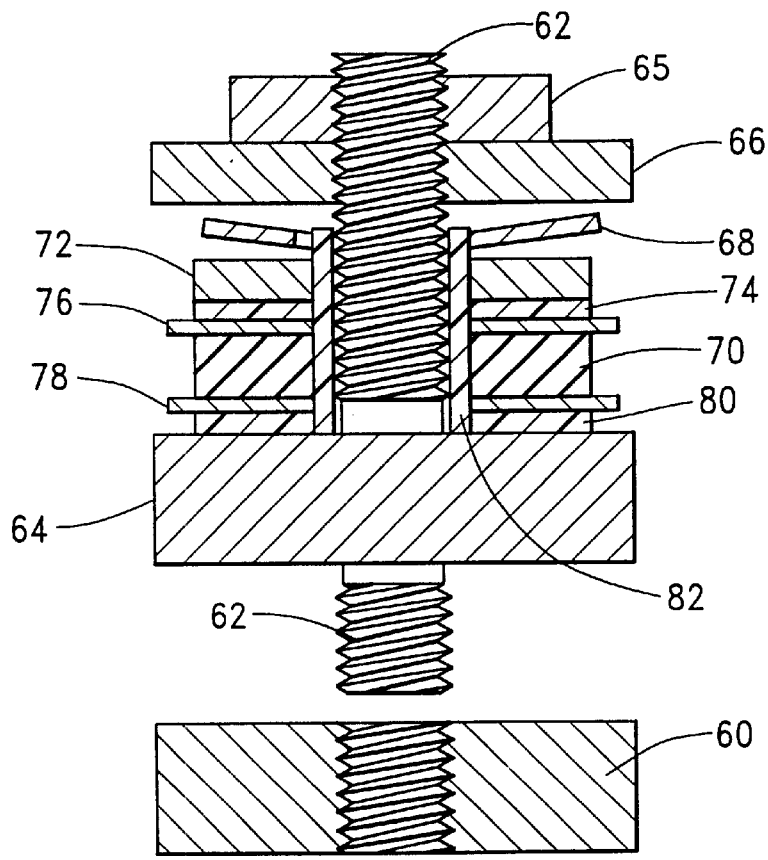
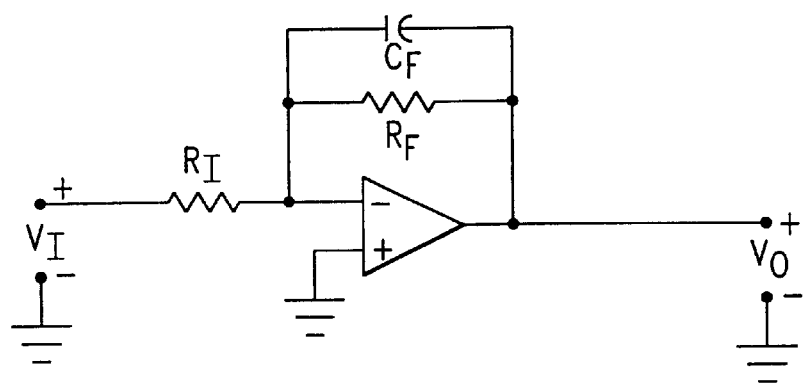
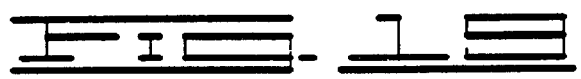

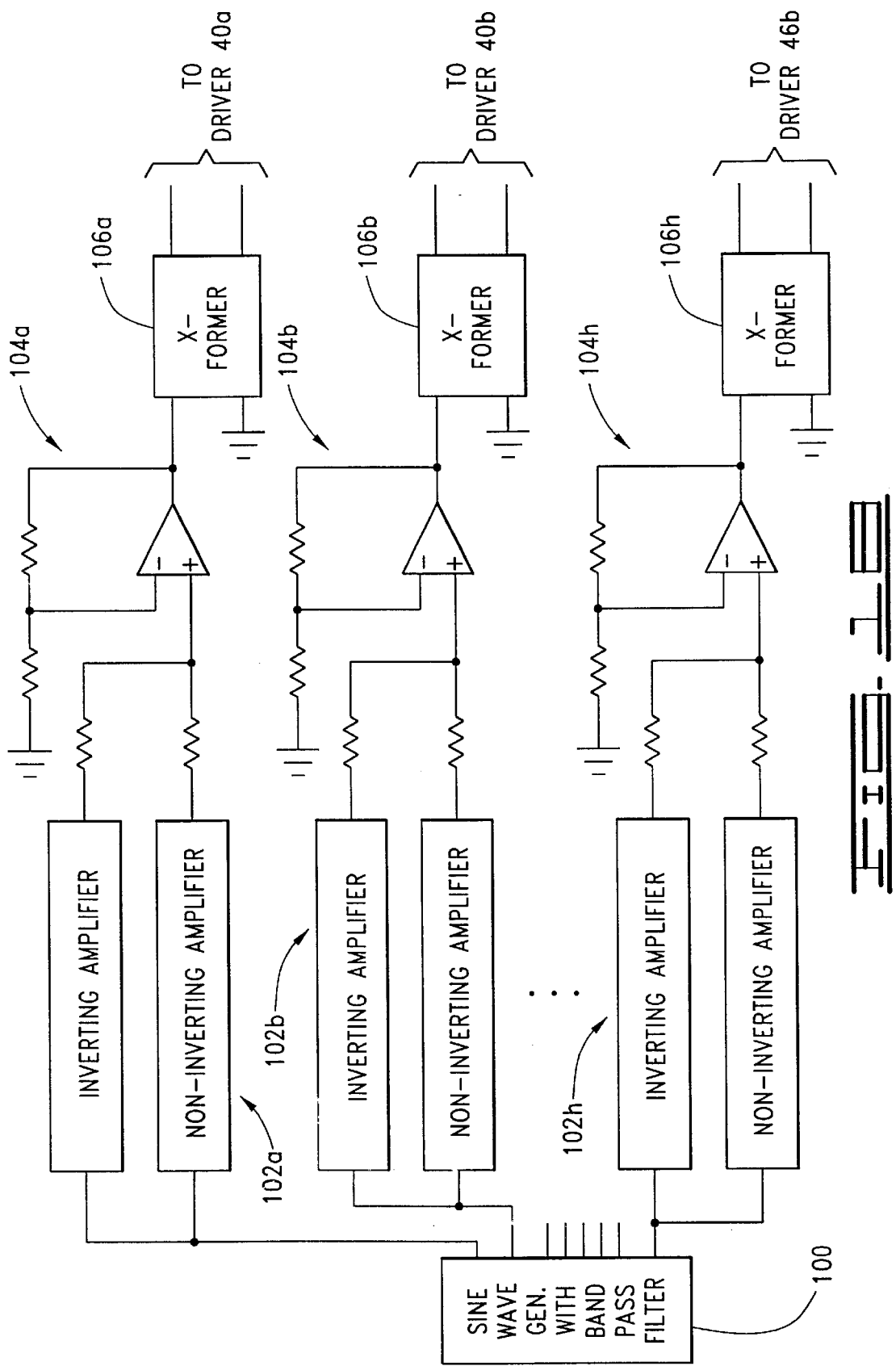

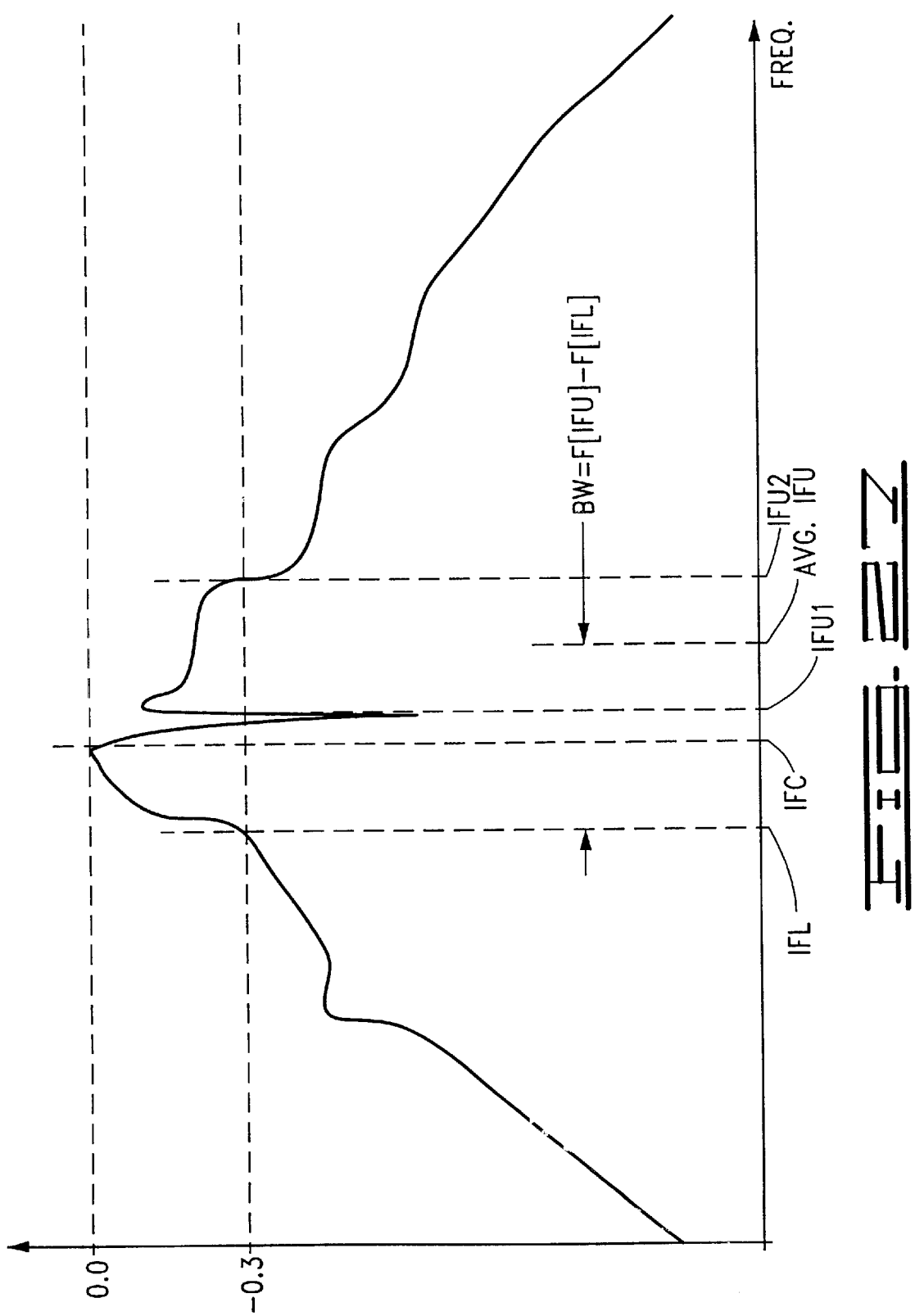

VIBRATIONAL FORCED MODE FLUID PROPERTY MONITOR AND METHOD

BACKGROUND OF THE INVENTION

This invention relates generally to fluid property monitors and monitoring methods. The present invention provides a fluid property monitor and method that use multiple frequency inputs in one or more vibrational modes to produce multiple resonant frequency outputs from which one or more fluid characteristics are determined. A particular application is to determine density of a cement slurry for use in an oil or gas well, but other applications are also contemplated, Cement slurry is mixed on rigs prior to delivery into wells. A cement slurry typically needs to have a particular density or density range to control downhole pressures during cementing. Slurry density is now typically monitored with nuclear densitometers; however, nuclear sources are forbidden in some countries. Also, density readings are sometimes erratic for foam cements at the wellhead after adding nitrogen. Other densitometers with fewer regulatory requirements (e.g., Coriolis devices) may disrupt flow and suffer from erosion by fluids. Still others (e.g., high frequency acoustic devices) may yield only small depths of investigation into the cross section of a fluid, which is unacceptable for fluids having radial gradients in pipes, for example. In other applications, density, compressibility and viscosity measurements are needed to monitor various flowing fluids, such as stimulation fluids and produced fluids downhole in wells.

A fluid monitor and monitoring method overcoming the aforementioned shortcomings are needed.

SUMMARY OF THE INVENTION

The present invention overcomes the above-noted and other shortcomings of the prior art by providing a novel and improved vibrational forced mode fluid property monitor and method. The monitor of the invention preferably imparts vibrations to a distinct system of a conduit and fluid, from which the monitor detects responses resulting from induced deformations of the conduit and the effects on the fluid in the conduit.

The vibrations used in the present invention relate to the modes of vibration of cylindrical shells. Although standing wave patterns for various such modes may be well known, the use and implementation of multiple modes and/or multiple frequency response in determining fluid characteristics as called for by the present invention are new. For a flexural mode, fluids in the bore of shells (to a first approximation) merely add mass loading, resulting in a decrease of resonant frequency. Radial mode resonance is affected by speed of sound which depends on density and compressibility. Torsional mode response couples primarily through the shear viscosity. The Q, the ratio of the center frequency divided by the difference between the upper and lower frequencies having amplitudes 3 dB smaller than the peak amplitude, of any of the resonances relates to energy dissipation, which relates to fluid shear viscosity, fluid bulk viscosity, other fluid dissipation mechanisms and structural energy loss mechanisms. Q's of the multimodes can be solved by multiple regression to estimate the contributions of each energy loss mechanism.

Such a fluid monitor and method may be used to measure various parameters, including density, compressibility and viscosity (and preferably measured from the same sample volume). Accuracy and response times of the invention preferably equal or exceed those of prior devices for monitoring corresponding fluids and parameters. The presence of multiple resonances permits the use of several center frequencies to improve the statistical accuracy of the determined characteristic. The invention has no nuclear sources, and it avoids device erosion.

The present invention applies to mixing and delivery of cement slurry, for example. As another example, the invention may also apply to evaluating stimulation fluids during delivery for enhanced reservoir production. Additionally, the invention may be used for combining with fluid velocity measurements to develop mass flow meters for various applications, including permanent downhole sensors.

Particular embodiments are described in following sections, but some other advantages of these include the following.

Fixed positions between transducers providing vibrational energy give relatively stable resonant frequencies even if the locations of end clamps supporting the test region conduit change slightly. The use of force couples avoids lateral forces on the end clamps that occur with unbalanced translational forces (forces on end clamps may cause errors in estimating true resonant frequencies, which frequencies are used in determining the desired fluid characteristic(s)).

Separate transducers for transmitting and receiving provide greater noise rejection than combined transmitter/receiver approaches; however, combined transducer embodiments are encompassed in broader aspects of the present invention.

Using a relatively large number of transmitters permits large amplitude vibrations to be generated. The dependence of amplitude on frequency gives the nonlinear behavior of fluid modulii which relates to the amount of gas in liquid. The invention, therefore, may be useful for estimating the amount of gas in liquids.

One embodiment permits transducers to be retrofitted on pipes that are already installed. The invention, therefore, can be designed with no interruption of the flow contours. Interruption of flow contours can cause erosion or improper mixing of multi-phase fluids.

In measuring at least density and using at least the flexural mode, the invention monitors the entire liquid cross section and therefore gives the average density of the total flow.

Another advantage is non-intrusive monitoring of density or other parameters. The radial flow profile in the test region conduit is unaffected by the device. This device requires no curvature of the conduit axis as in curved Coriolis flow meters. The maximum conduit diameter is only limited by the length of the monitor apparatus and the flexural wavelength. The larger the diameter, the longer the monitor apparatus. Active length of the activated conduit can be reduced relative to flexural mode length by using only one or more of the radial modes in implementing the present invention.

One definition of the present invention is as a fluid property monitor comprising a transducer assembly to impart multiple frequency energy to a conduit in multiple modes (e.g., flexural modes and/or radial modes), and to receive resonant frequency energy from the conduit, wherein the resonant frequency energy is responsive to the imparted energy, the conduit and a fluid in the conduit. In a particular embodiment, a radial mode includes a radial hoop mode and a radial oval mode.

The fluid property monitor can also be defined as comprising: a frequency signal generator connected to cause multiple frequency energy to be transferred to a conduit having a fluid to be monitored; and a spectral analysis signal processor connected to receive and process electrical signals generated in response to vibrations propagated through the conduit and the fluid in the conduit in response to transferred multiple frequency energy.

In a particular implementation the present invention provides a densitometer that comprises: at least four transducers disposed circumferentially relative to a location along a length of a conduit connected in-line in a flow path for a fluid to be monitored; a multiple frequency signal generator to provide one or more drive signals for the transducers to impart multiple frequency energy to the conduit; and a controller to connect the one or more drive signals to the transducers such that the transducers are operated to drive the conduit in any of a plurality of modes including a multiple frequency flexural mode and a multiple frequency radial mode.

In another implementation the present invention provides a coherent flow detector comprising first and second fluid property monitors disposed at respective first and second locations along a conduit for a fluid to be monitored. The first fluid property monitor includes a first transducer assembly to impart first multiple frequency energy to the conduit at the first location in multiple modes, including at least a flexural mode and a radial mode, and to receive first resonant frequency energy from the conduit, wherein the first resonant frequency energy is responsive to the imparted first multiple frequency energy, the conduit and a fluid in the conduit. The second fluid property monitor includes a second transducer assembly to impart second multiple frequency energy to the conduit at the second location in multiple modes, including at least a flexural mode and a radial mode, and to receive second resonant frequency energy from the conduit, wherein the second resonant frequency energy is responsive to the imparted second multiple frequency energy, the conduit and the fluid in the conduit.

A method of monitoring a fluid in accordance with the present invention comprises: imparting multiple frequency vibration-inducing energy to a conduit and fluid system, and sensing a plurality of frequency signals from the conduit and fluid system responsive to at least part of the imparted multiple frequency vibration-inducing energy. This method can also comprise: determining at least one characteristic of the conduit and fluid system in response to the sensed plurality of frequency signals. In a particular implementation, determining at least one characteristic includes using an averaging calculation with frequencies identified from the sensed plurality of frequency signals.

A method of monitoring a fluid in accordance with the present invention can also be defined as comprising: imparting multiple frequency energy at a first location of a conduit for a fluid to be monitored; imparting multiple frequency energy at a second location of the conduit; and detecting vibrational motion at a third location of the conduit, wherein the third location is between the first and second locations.

Another definition of the method of monitoring a fluid comprises: flowing a fluid through a conduit; driving at least one of one or more transducers disposed adjacent the conduit to impart energy to the conduit to deform the conduit in a flexural mode; driving at least one of the one or more transducers to impart energy to the conduit to deform the conduit in a radial hoop mode, driving at least one of the one or more transducers to impart energy to the conduit to deform the conduit in a radial oval mode; and generating signals, with at least one of the one or more transducers, in response to the driving steps.

Therefore, from the foregoing, it is a general object of the present invention to provide a novel and improved vibrational forced mode fluid property monitor and method. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 1 is a schematic illustration of a conduit with which a plurality of transducers are associated and driven to impart flexural mode vibrational energy to the conduit and a fluid inside the conduit.

FIG. 2 is a schematic illustration of the conduit with which the plurality of transducers are associated but now driven to impart radial mode vibrational energy to the conduit and a fluid inside the conduit.

FIGS. 5A–5F represent sequential stages within a cycle of the radial oval mode, wherein FIG. 5A represents a starting time, FIG. 5B depicts a maximum vertical elongation of the conduit, FIG. 5C depicts reversed drive polarity, FIG. 5D represents the conduit being driven back through its neutral shape, FIG. 5E depicts a maximum horizontal elongation of the conduit, and FIG. 5F illustrates the next reversed drive polarity to start the next cycle upon returning to the neutral shape of FIG. 5A.

FIG. 8 is a schematic illustration of moment arm assemblies connected to a conduit to impart flexural mode vibrational energy to the conduit.

FIG. 9 is a schematic representation of a single pair of transducers driven to impart a flexural mode to a conduit.

FIG. 10 is a schematic representation of the single pair of transducers driven to impart a radial mode to the conduit.

FIG. 11 is a schematic representation of a single combination transmitter/receiver transducer used to impart a flexural mode and a radial mode to the conduit and to receive responsive signals.

FIG. 14 illustrates the particular implementation driven to impart radial mode vibrations.

FIG. 15 is a block diagram of transmitting and receiving portions of the fluid property monitor of the present invention to be described as particularly correlated to the particular implementation of FIGS. 13 and 14.

FIG. 16 is an elevational view of a particular implementation of a transducer for the embodiment of FIGS. 13 and 14.

FIG. 18 is a schematic diagram of a mode controller circuit connected between the transmitting circuitry of FIG. 17 and the drive transducers.

FIG. 19 is a schematic circuit diagram of a signal conditioning circuit connected to a receiver transducer of the implementation of FIGS. 13 and 14.

FIG. 26 provides a densitometer frequency response plot with multi-layer Fibonacci searches employed to find center resonant frequencies in the mathematical analytical technique.

FIG. 27 illustrates part of a log normalized resonant signal for which half-power amplitude bandwidth is to be found in the mathematical analytical technique.

DETAILED DESCRIPTION OF THE INVENTION

Figure 3:
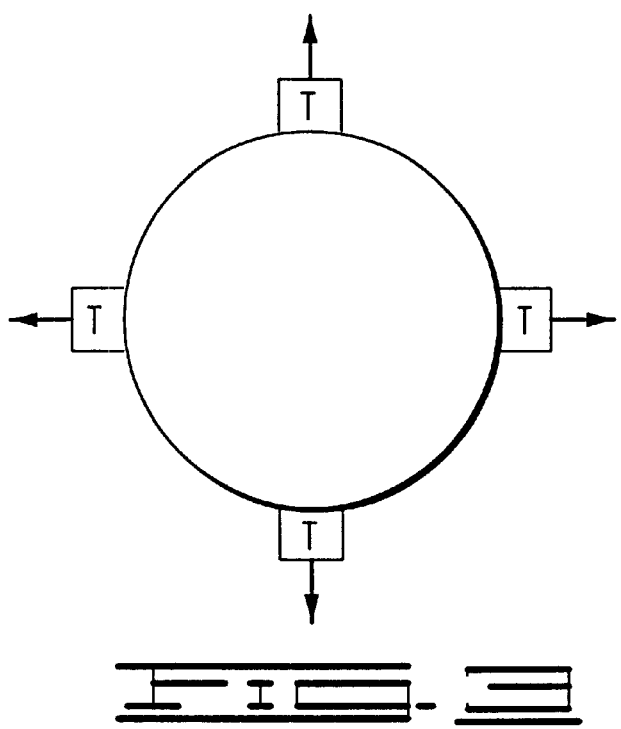
FIG. 3 is a schematic cross-sectional illustration showing a circumferential group of four transducers driven to provide a radial hoop mode.

The vibrational forced mode fluid property monitor and method of the present invention is for determining one or more various parameters for various fluids. Examples of such characteristics include density, compressibility, viscosity, flow velocity (including slip velocity, such as with two monitors used as a coherent flow detector), and foaming; and examples of fluids include cement slurries (including foamed slurries), stimulation fluids (e.g., fracturing fluids, acids), and drilling muds. The fluids can be static or flowing, and the fluids can be Newtonian or non-Newtonian and homogeneous or non-homogeneous. Use can be at various locations along a flow stream (e.g., before or after nitrogen injection for a foamed cement slurry) and with respect to various locations within the fluid (e.g., at the center, at the outer boundary, or an average across a cross section). To simplify the explanation of the invention, however, reference in the following description will primarily be made to monitoring density of a cement slurry; however, such specifics are not to be taken as limiting broader aspects of the invention.

The modes to which the present invention pertains include flexural, radial, and torsional, with the first two of preferred interest. At present, the most preferred embodiment uses a combination of flexural mode, radial hoop mode, and radial oval mode; however, any of the modes can be used alone or in combination with one or more of the other modes. When the monitored fluid has multiple phases (e.g., gas and liquid), flexural, hoop, and oval modes have different responses dependent upon the spatial distribution of the fluid phases. The flexural mode is more sensitive to fluid phases at the center of the stream than are the two mentioned radial modes. The hoop mode changes the volume of the flow conduit more than does the oval mode; therefore, the hoop mode is more sensitive to compressibility effects due to the presence of gases in liquids than are the flexural or oval modes.

Within the modes, multiple frequencies are used. Multiple frequency mechanical energy is applied or imparted to the conduit containing a fluid under test such that multiple frequency vibrations are induced in the conduit and fluid. Frequencies throughout or across the range of imparted frequencies are monitored and the relatively larger amplitude frequencies (typically the resonant frequencies) are used to determine the one or more parameters or characteristics (e.g., density). That is, the present invention senses for responsive signals related to at least some of the imparted frequencies, namely, for the resonant frequencies produced by corresponding input frequencies in the preferred embodiments.

For resonant frequencies associated with flexural modes, important factors include pipe structure, transducer mass, mass inside the pipe, and mass outside the pipe. For unchanging interior fluids, flexural mode frequencies can be calibrated to measure density (for example) of fluids outside the pipe. Previous flexural mode approaches position drivers for modes governed by the pipe length. Resonances based on pipe length have errors due to greater dependence on rigidity of end clamps. The forced mode approach of preferred embodiments of the present invention reduces end effects by having a central receiver with multiple drivers between the receiver and either pipe end. Driver axial locations are selected to enhance signals at receivers and minimize effects of end clamps. In FIG. 1 transducer pairs 2, 4 are equidistantly spaced from transducer pair 6. To provide the flexural mode, the pairs are driven as indicated by the respective arrows and then reversed in a cyclical manner. Although imparted from respective locations along the conduit, the cumulative effect applies vibratory energy to the conduit 8 as indicated by axial and boundary lines 10, 12, 14 (the illustrated displacements are exaggerated relative to the actual sizes and distances).

Resonant frequencies of radial modes depend on pipe structure, transducer mass, fluid inside and fluid outside the pipe, and fluid speed of sound. FIG. 2 shows the transducer pairs from FIG. 1 used to create a radial mode. The radial mode created by driving the transducers 2, 4, 6 as shown by the arrows in FIG. 2 and then reversing the drive in a cyclical manner propagates by deflecting the wall as shown in FIG. 2 by boundary lines 12, 14. The wall deflection at receiver transducer pair 6 is proportional to the deflection at driver transducer pairs 2, 4, but delayed in time. Driving two sets of drivers at equal symmetric distances relative to the radial plane at the receivers gives increased signal amplitude. Care must be taken if more sets of drivers at other axial distances from the receivers are used. The different propagation distances for other axial distances can give destructive rather than constructive interference at the receiver. The phase mismatch depends on speeds of sound in the fluid and in the conduit wall.

Figure 4:
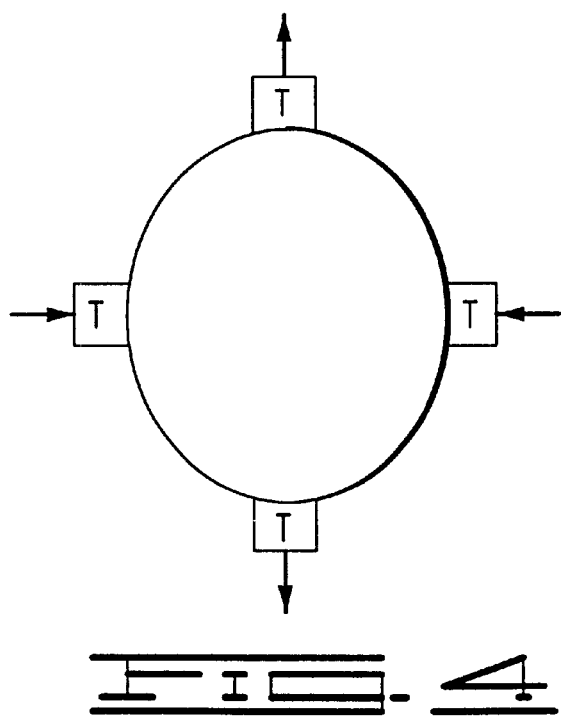
FIG. 4 is a schematic cross-sectional illustration showing the circumferential group of four transducers driven to provide a radial oval mode.
Figure 5:
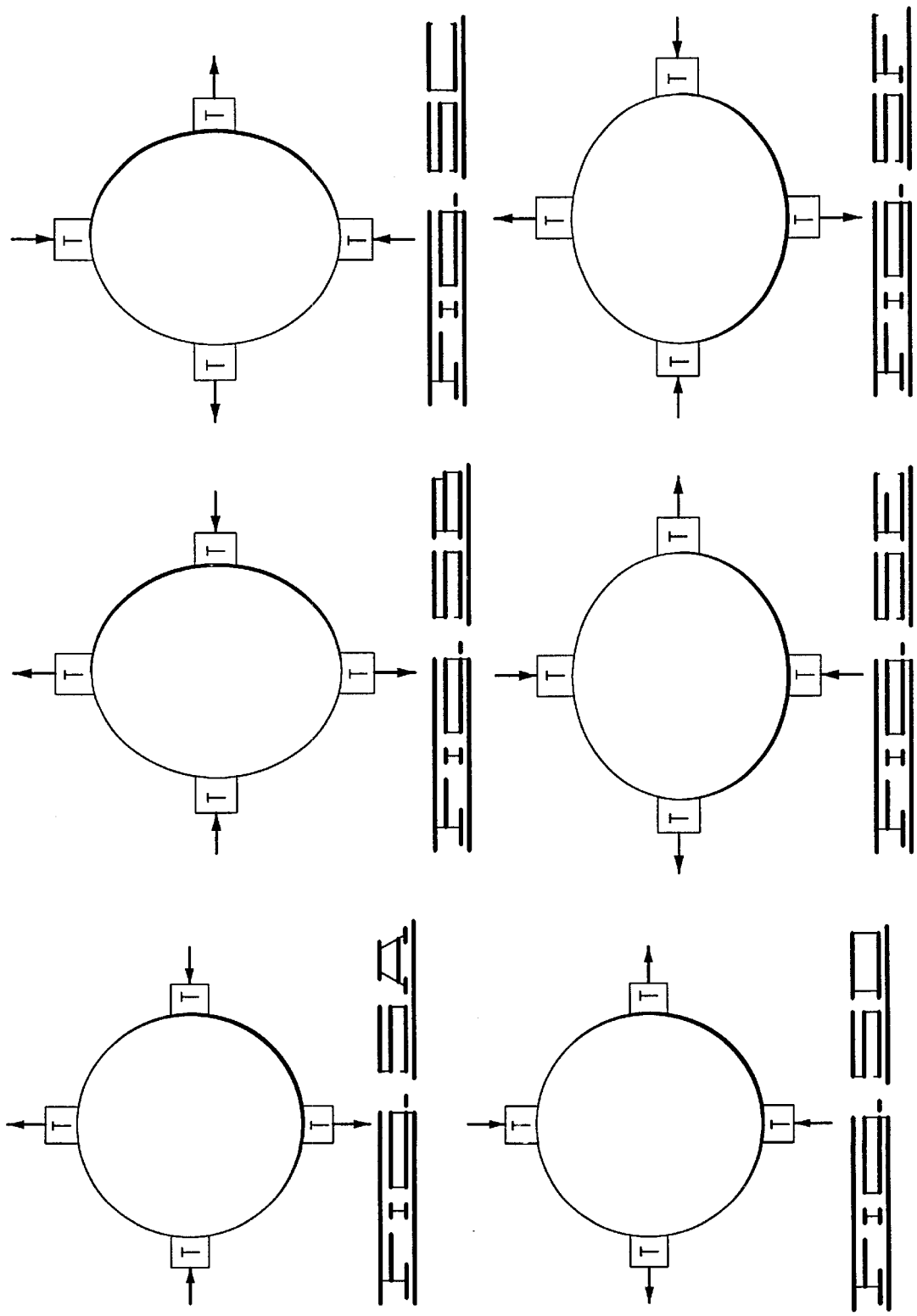

Two distinct radial modes are preferably generated with different electrical phases for the transducers. Consider four transducers T equally spaced circumferentially around the pipe as shown in FIGS. 3 and 4. Driving all four transducers T in phase causes uniform expansion and contraction of the circumference to define a radial hoop mode (FIG. 3). Driving one opposing transducer pair in phase and the other opposing transducer pair 180 degrees out of phase results in a radial oval mode (FIG. 4, and see FIGS. 5A–5F for an illustration of a cycle of the oval mode deflection of the conduit). These modes have fundamentals and overtones that give two distinct sets of resonant frequencies. Processing the sets independently gives greater accuracy of the density (or other characteristic) measurement.

Figure 6:
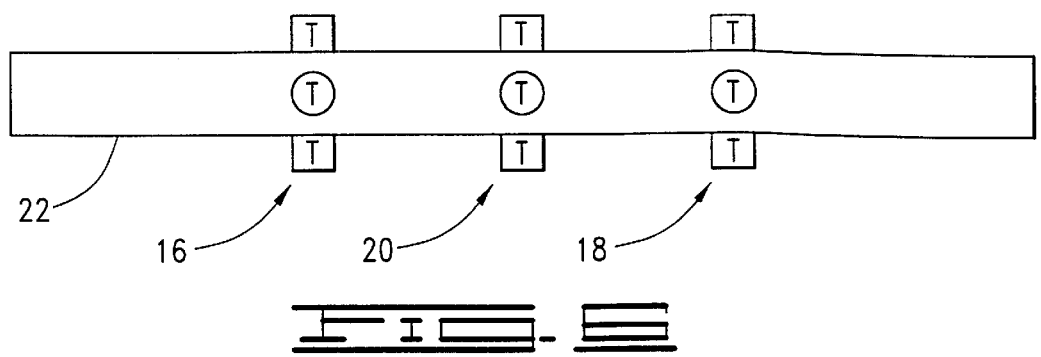
FIG. 6 is a schematic illustration of a conduit with which three sets of four circumferentially spaced transducers each are associated such that the transducers can be driven to impart flexural, radial hoop, and radial oval modes of vibrational energy to the conduit and a fluid inside the conduit.

FIG. 6 represents an embodiment with two sets 16, 18 of four circumferentially spaced driver transducers each. These are equally spaced axially from a centrally located set of four circumferentially spaced receiver transducers 20. By adjusting the relative electrical phasing of the individual driver and receiver transducers, one can vibrate the pipe 22 in flexural, hoop or oval mode. Preferably each of these modes is used and responsive frequencies detected to determine the desired parameter (e.g., density). Should end effects arise despite the symmetrical arrangement depicted, they would be more troublesome for the flexural mode than for the radial modes; however, the combination of flexural and radial modes permits using the radial modes to compensate the flexural mode for end effects.

When the transducers of FIG. 6 are driven as in FIG. 3 to create a hoop mode, the central axis of the conduit 22 is not moved as in the flexural mode, making the system relatively insensitive to density of material at the center. This mode has greater sensitivity to density of material at the wall. Because the area of the circle expands and contracts, the volume of the pipe changes and this mode is sensitive to changes in the net compressibility of non-homogeneous material anywhere in the pipe. When the transducers of FIG. 6 are driven as in FIGS. 4 and 5 to create an oval mode, the central axis of the pipe 22 is not moved. The area of the oval changes little, reducing the effects of compressibility.

Figure 7:
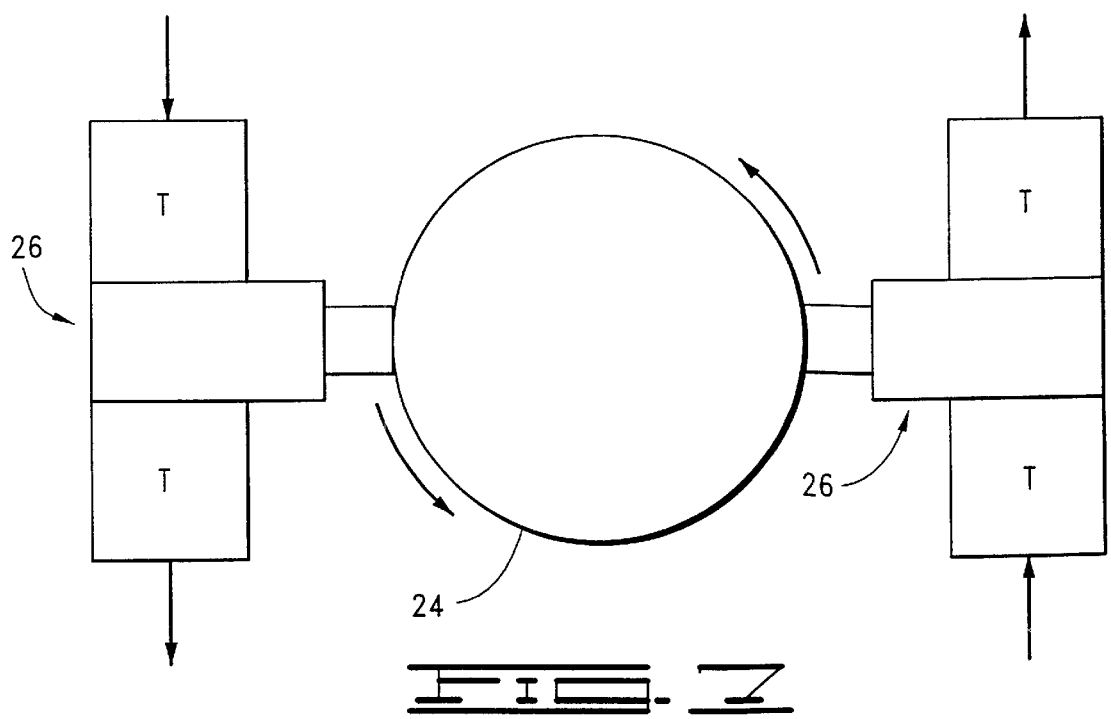
FIG. 7 is a schematic illustration of a moment arm assembly connected to a conduit to impart torsional mode vibrational energy to the conduit.

The foregoing are preferred modes of the present invention; however, another mode included in the present invention with regard to modes used in combination with each other is the torsion mode. For resonant frequencies associated with torsion modes, important factors include pipe structure, transducer mass, mass and shear viscosity of fluid inside the pipe, mass and shear viscosity of fluid outside the pipe, fluid compressibility, and transducer location. FIG. 7 shows a moment arm arrangement, including transducers T and clamped moment arm members 26, that imparts torsional motion to pipe 24. One of these arrangements placed at the axial center of the pipe will create torsional displacement of the pipe wall. The receiver must sense torsional displacements. Transverse oriented accelerometers, transverse poled piezoelectrics or torsion arm transducers are acceptable. Torsion modes couple weakly through viscosity and so a nontorsional mode may obscure effects of the weak coupling; therefore, a torsion driver should be designed to avoid non-torsional excitation modes and a receiver should be designed to reject small non-torsion modes created by torsion drivers.

The moment arm arrangement can also be used to induce the flexural mode as illustrated in FIG. 8. The forced mode generated in this device can be developed by applying a set of equal and opposite couples at equal distances from the center of the device. The moments can be created by mounting the transducers on moment arms 26' attached to the pipe as shown in FIG. 8. The transducers oscillate in the axial direction of the pipe and thus do not contribute any force in the transverse direction relative to the pipe. The moment imparted by the oscillation of the transducers and the flanges bends the pipe while allowing vibration in preferred natural modes. Such a vibration is represented in FIG. 8 by center line 28. The pipe is forced to observe a change in bending moment at the clamping flanges. The pipe response to the driving frequency is a strong function of the pipe contents, since the pipe vibrates in its natural modes. To obtain an antinode at the receivers, the drivers must produce pipe wall motions that are symmetric relative to a radial plane at the centered receivers. The two moments shown in FIG. 8 acting in opposite directions and located on opposite sides of the center remove any asymmetric mode shapes and allow only symmetric modes to exist. The centered antinode of symmetric modes can be easily detected by the receivers mounted at the center of the pipe. The centered nodes of asymmetric modes, in contrast, have no transverse deflections at the center of the pipe, and hence give no signals in the receivers. A receiver similar to that for the moment arm drivers in FIG. 7 is used to detect centered nodes of asymmetric modes.

FIG. 8 shows transducers on moment arms. An alternative design includes a flange that allows resonance at desired frequencies using either normal or bi-morph piezoelectric elements.

The foregoing has been described with reference to more than three transducers. In this particular context, the fluid property monitor of the present invention comprises a receiver disposed relative to a length of conduit to detect vibrational energy of a location of the conduit (e.g., a central location as illustrated in FIGS. 1, 2, 6, and 8). This fluid property monitor also comprises a first transmitter to impart vibrational energy to the conduit. The first transmitter is disposed relative to the conduit at a location spaced along the length of the conduit in a first direction from the receiver. This fluid property monitor still further comprises a second transmitter to impart vibrational energy to the conduit. The second transmitter is disposed relative to the conduit at a location spaced along the length of the conduit in a second direction from the receiver such that the receiver is between the first and second transmitters. For examples of these transmitters, see FIGS. 1, 2, 6, and 8.

Although the foregoing represents presently preferred embodiments of the present invention, one can create and receive at least flexural and radial modes with a single transducer pair 30a, 30b mounted relative to conduit 32 as illustrated in FIGS. 9 and 10; however, the interpretation of the respective modes may be difficult if the range of density (or other measured parameter) causes overlapping of the response ranges for the respective modes. Furthermore, even a single combination transmitter/receiver transducer 34 can be used as illustrated adjacent conduit 36 in FIG. 11. This capability of generating many modes with a single transducer results because many modes cause radial movement of the pipe surface, and a transducer receiving signals related to the radial movement detects the modes. Transducers generating forces in the radial direction excite the modes if driven at the resonant frequency (transducers placed at nodes or other locations giving no radial wall motion cannot receive or generate the corresponding modes). In view of these options, what is needed at a minimum for the fluid property monitor of the present invention is a transducer assembly to impart multiple frequency energy to a conduit in one or more modes (e.g., flexural and/or radial modes), and to receive resonant frequency energy from the conduit, wherein the resonant frequency energy is responsive to the imparted energy, the conduit and a fluid in the conduit. In terms of a method, this includes imparting multiple frequency vibration-inducing energy to a conduit and fluid system, and sensing a plurality of frequency signals from the conduit and fluid system responsive to at least part of the imparted multiple frequency vibration-inducing energy. In response to the sensed plurality of frequency signals, at least one characteristic of the conduit and fluid system is determined. As will be explained below, determining at least one characteristic includes using an averaging calculation with frequencies identified from the sensed plurality of frequency signals. In the embodiments of FIGS. 1, 2, 6 and 8, for example, multiple frequency energy is imparted at respective locations along the conduit and resultant vibrational motion is detected at another location of the conduit in between the first-mentioned locations.

Figure 12:
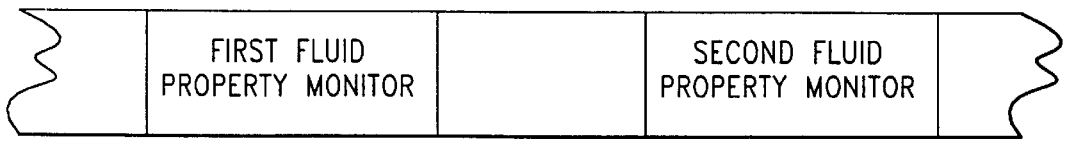
FIG. 12 is a schematic and block representation of a coherent flow detector of the present invention comprising two fluid property monitors of the present invention.

The present invention also provides two or more fluid property monitors as described above to create a coherent flow detector that can indicate the speed at which inhomogeneities move relative to the monitors for multiphase fluids. Such a coherent flow detector comprises: a first fluid property monitor disposed at a first location along a conduit for a fluid to be monitored, and a second fluid property monitor disposed at a second location along the conduit. In one implementation, the first fluid property monitor includes a first transducer assembly to impart first multiple frequency energy to the conduit at the first location in multiple modes, including at least a flexural mode and a radial mode. The first transducer assembly is also to receive first resonant frequency energy from the conduit, wherein the first resonant frequency energy is responsive to the imparted first multiple frequency energy, the conduit and a fluid in the conduit. In such implementation the second fluid property monitor includes a second transducer assembly to impart second multiple frequency energy to the conduit at the second location in multiple modes, including at least a flexural mode and a radial mode. The second transducer assembly is also to receive second resonant frequency energy from the conduit, wherein the second resonant frequency energy is responsive to the imparted second multiple frequency energy, the conduit and the fluid in the conduit. This is schematically illustrated in FIG. 12.

A Particular Implementation

Figure 13:
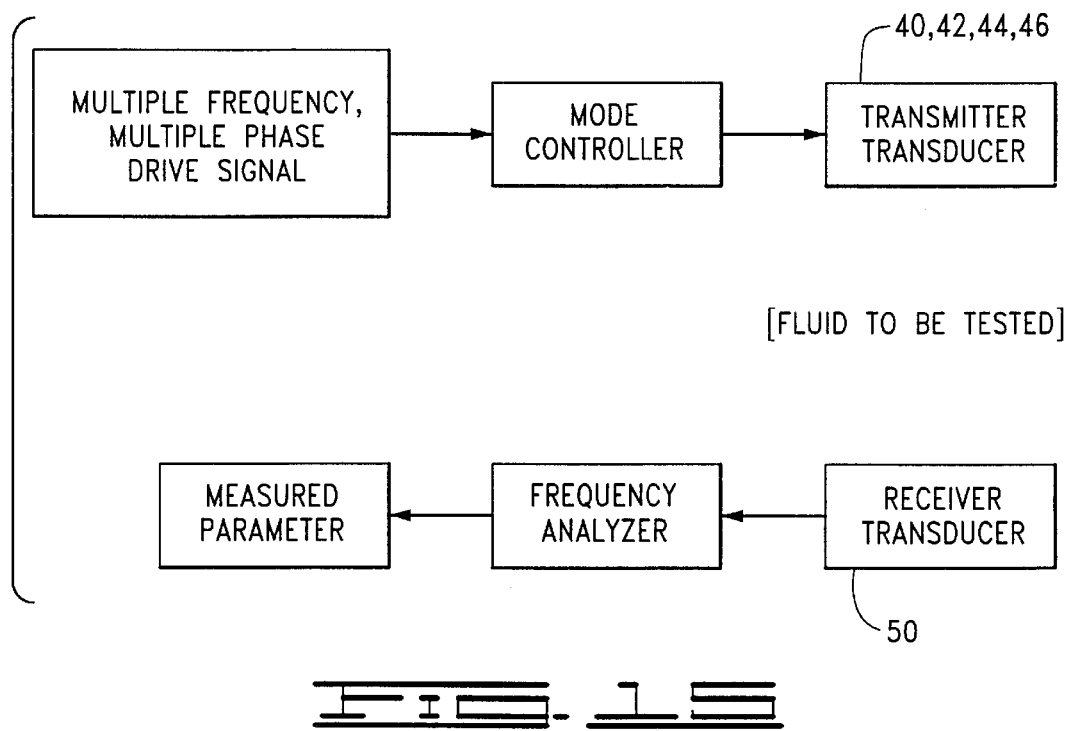
FIG. 13 illustrates a particular implementation having five pairs of transducers mounted on the conduit and driven to impart flexural mode vibrations.

A specific fluid property monitor which has been built and used in internal experimentation referred to hereinbelow is represented in FIGS. 13 and 14. Transducers 40*a*, 40*b*, 42*a*, 42*b*, 44*a*, 44*b*, 46*a*, 46*b* are placed along conduit or pipe 48 to give balanced forces at least in flexural mode. For flexural mode, two pairs of outer transducers (40, 46) produce forces in the opposite direction to two pairs of inner drivers (42, 44) as represented in FIG. 13. In FIG. 13, the four pairs 40, 42, 44, 46 produce two couples, one couple on either side of centered receiver transducers 50*a*, 50*b*. Each couple has no net translational forces, only rotational forces. This feature means that end clamps experience superpositions of waves from two couples. Spacing between couples and between each couple and pipe ends are selected to minimize end effects.

For radial mode, at least one of the pairs 40, 42, 44, 46 is used, wherein the respective transducers of the pair(s) are cyclically driven towards and away from each other as depicted in FIG. 14 for pair 42. If only one pair is used, the other driving transducers are quiescent. The behavior in FIG. 14 can be achieved by an electrical system that allows the electrical phase of each transmitter and each receiver to be actuated either in phase or 180° out of phase with respect to an oscillator driven at the selected modal resonance frequency.

When the conduit and transducer assembly of FIGS. 13 and 14 is to be used, the driver transducers are connected to receive one or more multiple frequency, multiple phase drive signals provided from a multiple frequency signal generator through a mode controller as indicated in FIG. 15. The controller connects one or more drive signals to one or more of the drive transducers so that the transducers impart the multiple frequency energy to the conduit in the appropriate mode(s). The electrical outputs from the receiver transducers responding to what has happened to the imparted energy in the conduit and fluid system are provided to a frequency analyzer from which one or more measured parameters is determined as also indicated in FIG. 15. The frequency analyzer is a signal processor that provides spectral analysis of the received signals, particularly resonant frequency energy detection responsive to the imparted energy, the conduit and the fluid in the conduit. The features indicated in FIG. 15, including the conduit 48 (FIGS. 13 and 14) and the transducers 40, 42, 44, 46, 50, will next be described in more detail for this particular implementation of a fluid property monitor of the present invention.

The conduit 48 can be a section of pipe already in place and containing a flowing fluid. Transducers can be clamped to or otherwise operatively associated with the outside of the pipe. The system can be calibrated by flowing materials with known density through the pipe. Alternatively, a flanged section can be installed which has been pre-calibrated. The conduit 48 can be a stand-alone test chamber or pipe segment or other suitable fluid container.

Because large amplitudes are desired to interpret the nonlinear response of the liquid modulii, the preferred embodiment has distributed transducers to minimize pipe distortion. The large forces for a single driver could cause local distortion of the pipe and so this is not preferred, but, as stated above, the present invention can be implemented with a single transducer.

In the implementation of FIGS. 13 and 14, to avoid coupling changes with aging, the preferred approach is to weld nuts to fasten transducers to the pipe; however, other attachment techniques can be used (e.g., clamping), and non-contacting transducers can be used. An example of a non-contacting transducer is a permanent magnet attached to the pipe and a drive coil mounted on a stationary frame. The coil is energized at the driving frequency.

Referring to FIG. 16, each of the transducers used in the particular construction related to FIGS. 13 and 14 mentioned above is a studded transducer that attaches to a respective nut 60 welded to the conduit 48. A cylindrical threaded post 62 extending from both sides of a stainless steel base 64 has a locking nut 65, a tensioning nut 66, and a Bellville spring washer 68 mounted on it to press a piezoelectric member 70 towards the base 64. The washer 68 acts against a tungsten washer 72 which provides inertial backing for the piezoelectric 70. The washer 72 lies against an insulating washer 74 disposed adjacent a negative electrode 76 positioned against one side of the piezoelectric member 70. A positive electrode 78 and an insulating washer 80 are between the other side of the piezoelectric member 70 and the base 64. The portion of the post 62 extending on this side of the base 64 passes axially through the elements as shown in FIG. 16. An insulating sleeve 82 is between this portion of the post 62 and the elements up to the tensioning nut 66. The other portion of the post 62 extends from the opposite face of the base 64 to screw into the nut 60.

The insulating washers 74, 80 on the transducers functioning as receivers give common mode rejection of electrical crosstalk from the drivers. If added rejection is needed, a stack of piezoelectrics can be used with the top side of the top element having the same electrical polarity as the bottom side of the bottom element. The greater the number of elements in the stack, the better the rejection of capacitive electrical crosstalk.

If an embodiment using this particular construction is retrofitted on an existing pipe that precludes welded nuts, the stainless steel base 64 can be made without the lower (as viewed in FIG. 16) stud and contoured to the outside diameter of the pipe. The tensioning and locking nuts 65, 66 can be replaced with a clamp that encircles the pipe. The clamp pulls together two transducers mounted on diametrically opposite sides of the pipe. The transducer placement would be the same as that in FIGS. 13 or 14, but the pairs of transducers would be secured by encircling clamps that pressed inward on the Bellville washers instead of by studs in welded nuts.

If the positive (+) receiver in FIG. 13 has positive polarity on the outside of the piezoelectric stack and the negative (−) receiver has negative polarity, then these receivers attach in parallel to the electronic amplifier in the frequency analyzer represented in FIG. 15. The parallel configuration further reduces capacitive crosstalk. Because receivers have stacks of positive and negative polarities, radial mode vibrations are rejected. sensitivity to flexural mode vibrations, however, is unaffected. This configuration reduces capacitive crosstalk and mechanical detection of undesired radial modes. (If switching from flexural to radial mode is desired, receiver transducers are individually connected to separate amplifiers.)

If translational mechanical vibrations interfere with the flexural motion, a second pair of receivers can be mounted at an odd number of wavelengths from the illustrated receiver pair 50. The locations of the positive and negative receivers for this second pair are interchanged diametrically. All receivers are attached electrically in parallel. The four receivers should have electrical rejection of capacitive crosstalk and mechanical rejection of radial modes and translational modes. This wiring configuration allows cancellation without the noise of separate amplifiers. Amplifier noise comes after the electrical subtraction. It also avoids the dynamic range problems amplifiers have in subtracting large signals that are almost equal. This four receiver configuration may be needed for environments with large mechanical shocks but may be unnecessarily expensive for normal conditions. If the amplifier dynamic ranges are inadequate for subtraction, separate sets of receivers for flexural, for hoop and for oval mode can be used to obtain subtraction before amplification.

Transmitting Circuitry

For the transducers used as drivers in the particular implementation being described with reference to FIGS. 13–15, the transducer drive circuitry provides the multiple frequency, multiple phase energy signals and mode control indicated in FIG. 15. Circuitry for generating the drive signals will next be described with reference to FIG. 17, and then an implementation for the mode controller will be described with reference to FIG. 18. In this implementation power for the circuitry is unipolar (e.g., +12 VDC from a vehicle battery), but split power (+/−15 VDC in a specific implementation) is used for piezoelectric transducer drive.

Figure 17:
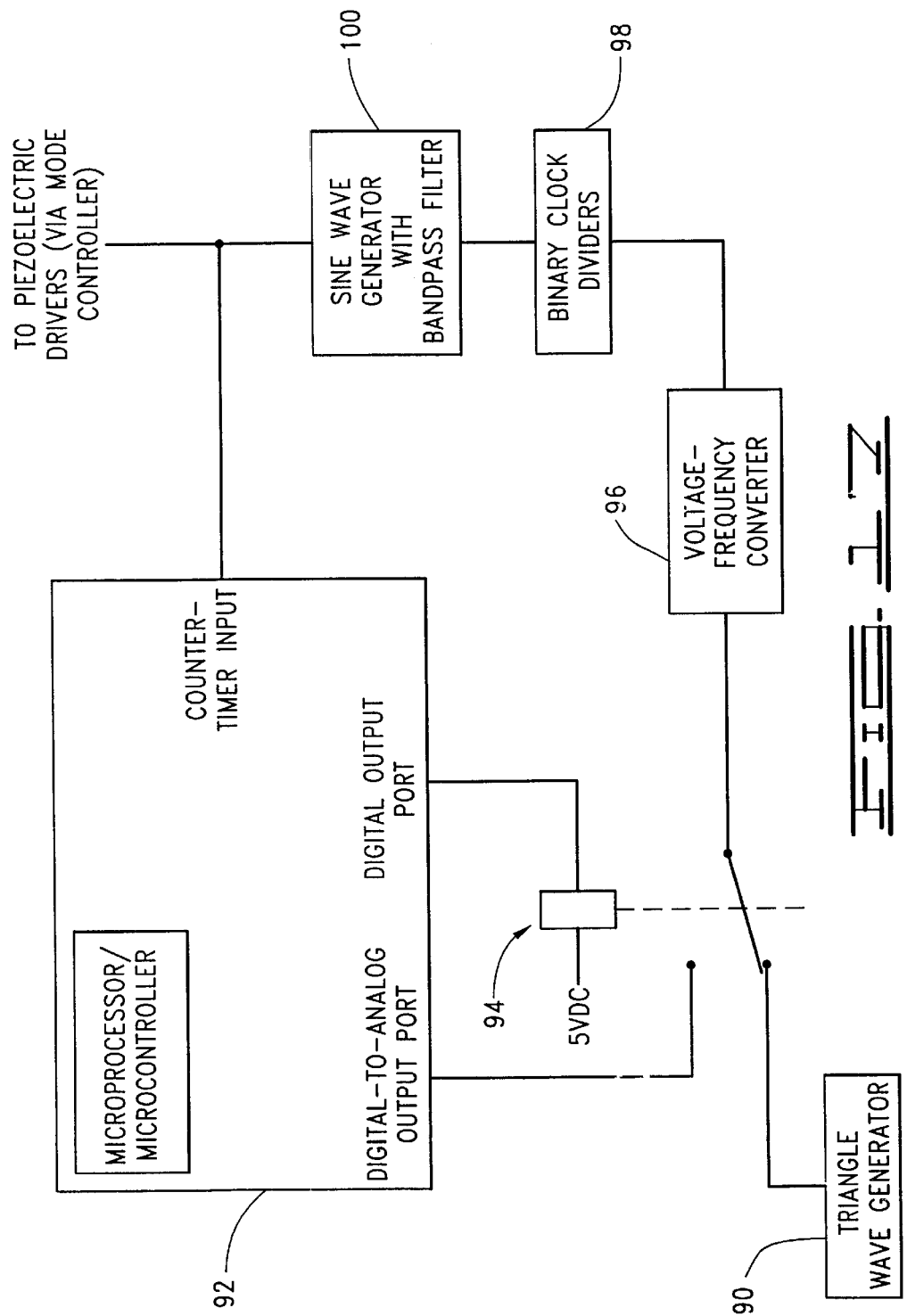
FIG. 17 is a block diagram of transmitting circuitry to drive the piezoelectric transducers of the implementation of FIGS. 13 and 14.

FIG. 17 depicts a particular implementation for generating sine wave signals used to drive the transducers associated with the conduit in which the fluid to be tested is contained or through which the fluid to be tested flows. A triangle wave is provided from a triangle wave generator 90. An alternative control signal can be provided from a programmed microprocessor circuit, or microcontroller, 92 (e.g., Z-World BL1700-based circuit). Selection of the control signal is made by the microcontroller 92 via its operation of a solenoid switch 94 as apparent from FIG. 17. The selected control signal is input to a voltage-to-frequency converter 96, the frequency output from which is divided to a desired level by binary clock dividers 98. The output of the circuit 98 drives a sine wave generator (with bandpass filter) 100. The output of the sine wave generator 100 is provided to the mode controller. This output from the sine wave generator 100 is also provided to the microcontroller 92 for monitoring and synchronization.

In the particular embodiment, the foregoing circuitry is designed and operated to generate drive signals that vibrate the conduit 48 within the range between about 100 hertz and about 20 kilohertz (kHz), and more preferably between about 3 kHz and about 14 kHz. Such frequencies can be obtained by providing one or more signals having a frequency that is swept through the particular range used or by providing multiple individual signals each having a respective frequency within the range or by providing a composite multiple frequency signal (e.g., a multiple frequency pulse) or a combination of the foregoing.

Depicted in FIG. 18 is an embodiment of the mode controller for the particular implementation being described with reference to the general block diagram of FIG. 15. The output signal from the sine wave generator 100 is filtered to remove direct current (DC) biases and attenuate any high frequency noise above 14 kHz for the aforementioned preferred range. In this context, filtering can be purely passive because gain control is not necessary. This output signal is split eight ways (i.e., provided in parallel to eight inputs) and routed through parallel inverting/non-inverting amplifier sets 102a, 102b, . . . 102h (e.g., model HA-2400 devices in a specific implementation) that offer gain and phase control. Outputs from these amplifier sets are coupled together and routed to power operational amplifier circuits 104a, 104b, . . . 104h (e.g., model OPA544 devices in a specific implementation). Final drive signals are then routed through transformers 106a, 106b, . . . 106h to the eight piezoelectric driver transducers 40, 42, 44, 46 of FIGS. 13 and 14. Each transformer 106 preferably adequately matches both source (power op amp 104) and destination (transducer) impedances, offers minimal distortion over the specified frequency range, and handles the estimated six-watt (W) power load with reasonable size, weight, and cost. Phase, and thus mode, control occurs by the microcontroller 92 controlling which amplifier within a set 102 is operational to process and output the input drive signal. Different combinations of in-phase and/or 180° out-of-phase signals can be provided.

Advantages of this approach include the following. For phase control, switching between amplifiers 102 occurs at low power rather than at high power which should reduce noise tendencies. Supply current demands are met on the low voltage side, which is more easily accomplished than on the high voltage side.

Although the foregoing is preferred, an alternative is to use high voltage operational amplifiers for final transducer drive, powered by a high voltage power supply. This would eliminate the audio transformers 106 of FIG. 18, but then needed high voltage linear power supplies rated at roughly 0.1 amp (A) rms per transducer (0.8 A rms total) at 60–70 volts (V) rms would be very large, expensive items with a large power transformer included.

Receiving Circuitry

Turning now to the receiving side of the presently described particular implementation for the embodiment of FIG. 15, a high impedance isolation amplifier can be used for piezoelectric receiver signal conditioning. That is, the output of a receiver transducer connects to a signal conditioning amplifier, and one type of such amplifier is a high impedance isolation amplifier. For example, input impedance on the order of 80 megaohms provides crystal isolation, with signal voltage amplification available through a resistor pair ratio. Another type of amplifier, and one that is presently preferred, is a low input impedance current amplifier. An example of a receiver amplifier circuit is shown in FIG. 19. Other conditioning components include a full-wave rectifier, differential amplifier, and low-pass integrator. The signal output from the receiver circuit is processed for frequency analysis which leads to measurement of the parameter(s). Such analysis and interpretation into parameter or characteristic measurement is described further below with regard to processing techniques, which can be implemented using the microcontroller 92 of FIG. 17. The resultant measurement can be output by any suitable means; non-limiting examples include a display screen (e.g., a touch screen which also allows user input), a 4–20 mA interface to provide data in this conventional format (as in a radioactive densitometer), and a serial interface (such as for digital data transfer).

Test System

A test system for a fluid property monitor of the type shown in FIGS. 3 to 6 was suspended vertically in the laboratory with a valve on the bottom. The tube was filled with the valve closed. Resonant frequencies were measured, and the tube was emptied by opening the valve. The electrical driving oscillator was controlled manually to find resonant frequencies for a variety of liquids. For the oval mode in FIG. 5, the results in FIG. 20 were obtained.

Figure 21:
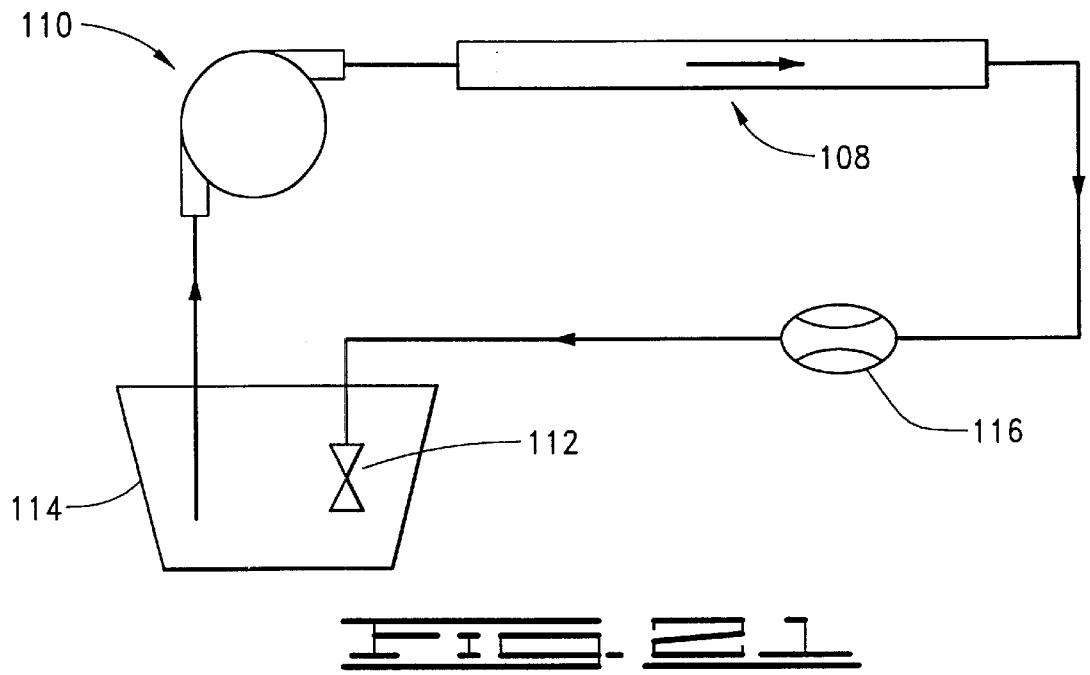
FIG. 21 is a schematic diagram of a test flow system incorporating the implementation of FIGS. 13 and 14.

A second fluid property monitor 108 (FIG. 21) was used to gauge resonant frequency and bandwidth in a flowing system. This monitor used the flexural mode shown in FIG. 13. FIG. 21 shows a centrifugal pump and an alternating current (AC) induction electric motor 110 with adjustable pulleys allowing for three different pump speed ranges. Flow rate adjustment within each pump/motor speed range was achieved by adjusting the loop restriction via a valve 112. This allowed the motor to run at constant speed. Connection hoses and a reservoir 114 were also included as apparent from the drawing. To complete the flow loop, a Halliburton turbine flow meter 116 was acquired, and various pipe fittings were purchased and assembled. Water (specific gravity 1.0) was pumped from the reservoir 114 by the motor/pump 110, through the fluid property monitor 108 and the flow meter 116, and back into the reservoir 114.

Two dependent variables were of primary interest with flow rate the independent variable. A 0.5-in. Halliburton turbine flow meter was used with conversion constant 875 pulses per gallon. Flow rate (gallons per minute) was computed using this constant along with frequency measurements taken during flow tests. Resonant frequencies near 6200 Hz, 9000 Hz, and 12000 Hz were measured by centering their resonant spike on an oscilloscope graticule and measuring the associated voltage-controlled oscillator (VCO) signal voltage. System calibration data was used to convert VCO amplitudes to frequency. Some measurement uncertainty was inherent, but of primary interest was to see if resonant frequencies had any flow rate dependence. Also measured were the actual resonant spike voltage amplitudes. Of interest was to see how amplitudes were maintained through a series of tests.

Figure 22:
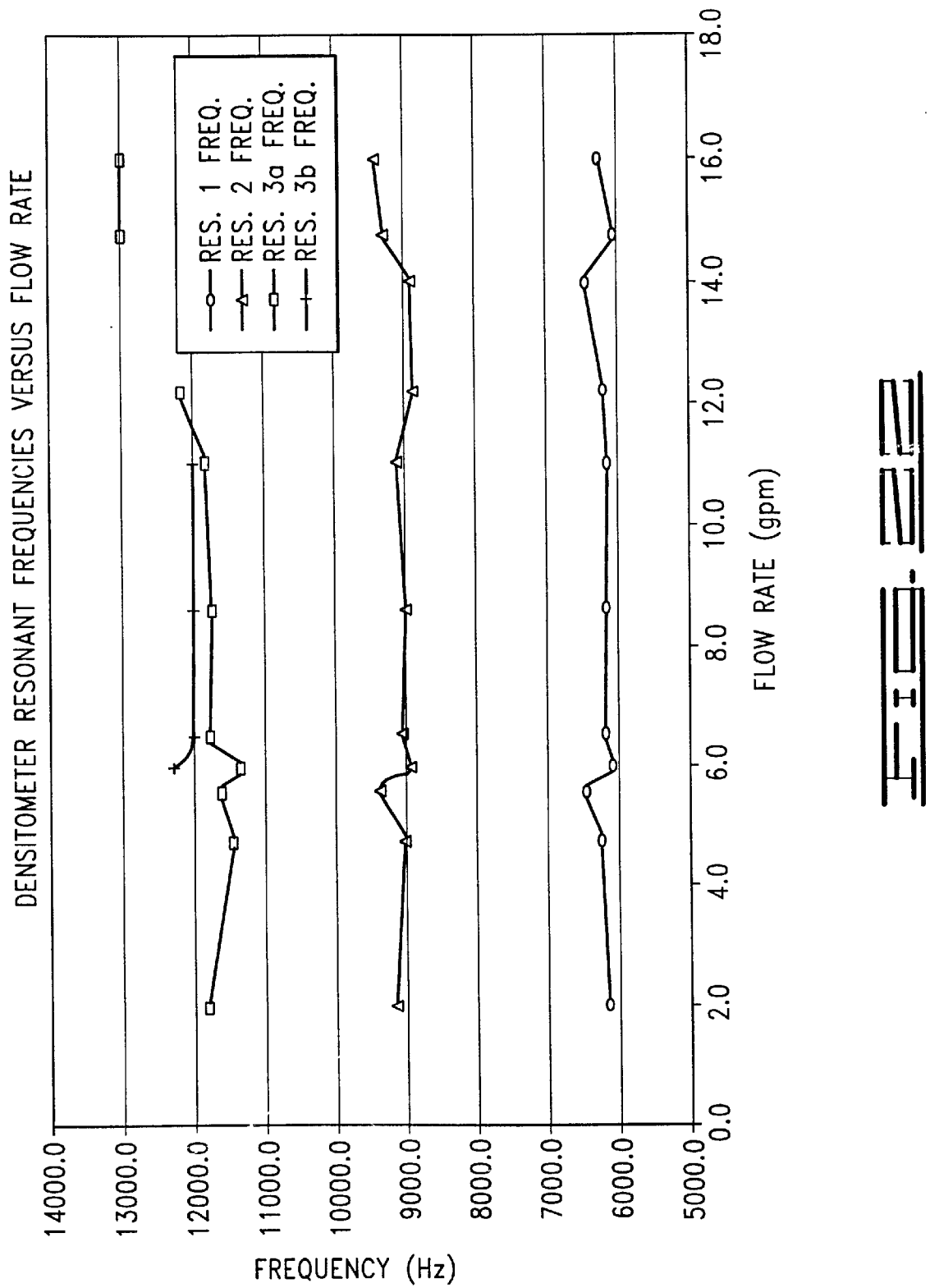
FIG. 22 shows graphs of resonant frequencies detected during a test in which flow rate of the fluid changed in the system of FIG. 21.

Flow rates from 2 gpm (gallons per minute) to 16 gpm were achieved. The graphs of FIG. 22 show that frequency for the most part held constant through the flow rate range. Aeration became more significant as flow rates increased, possibly due to leakage through a pump seal. One expects frequency to increase with percent aeration (overall fluid density decreases), but only the 12000 Hz trace exhibited that behavior. Average frequencies were 6228, 9076, and 12053 Hz.

Figure 23:
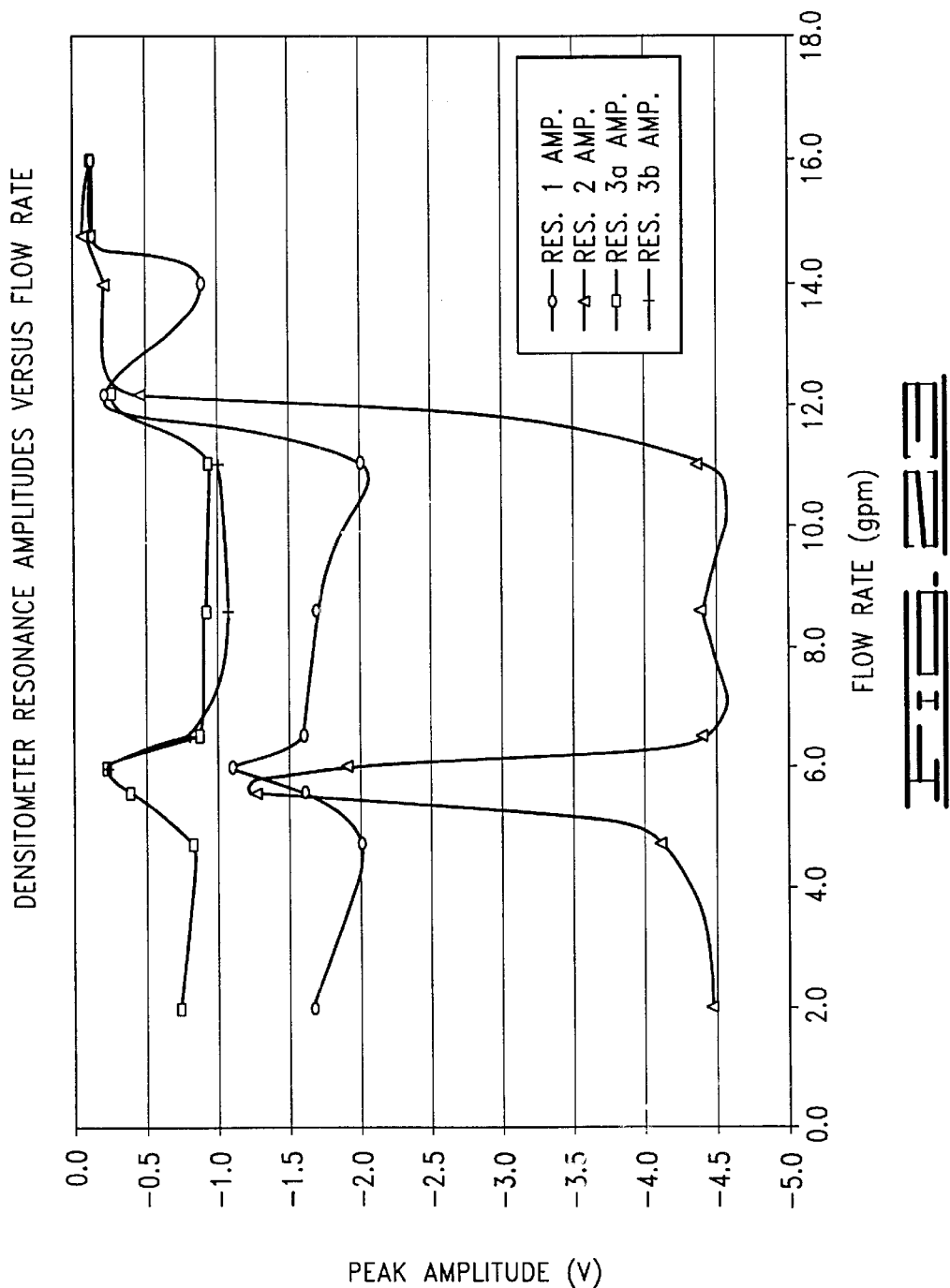
FIG. 23 shows graphs of resonant signal amplitudes across the flow rate range.

FIG. 23 shows much variation in signal amplitude through the flow range. This was first believed to be exclusively a product of aeration. Above 12 gpm, aeration was significant and all signal amplitudes decayed greatly. At approximately 5.9 gpm, however, all signal amplitudes were attenuated through a narrow band. Possible causes for this behavior are at present unknown; however, flow velocity at 5.9 gpm was approximately 6.8 in./sec., and it is possible that 6.8 in./sec was coincident with some critical flow velocity.

The foregoing illustrates that in the present invention the frequency response for a given spacing of transducers is determined by sweeping driving frequency and observing center frequencies of resonances. A number of resonance peaks will be observed, representing various reverberation modes of the entire structure. Peaks with largest amplitudes and largest mechanical Q's are observed for various calibration fluids from air to the most dense fluid to be measured. The resonances having the most stable amplitudes and Q's for the range of calibration densities should be used for interpreting density (or other fluid characteristic). The percentage change of center frequency versus characteristic is relatively stable and can be calibrated for each resonance peak. For improved accuracy, the characteristic's measurement can be obtained from a statistical fit of several resonant peaks. A statistical estimate based on the center frequencies of standing waves may give greater accuracy than resonance peaks individually.

Increasing vibrational amplitude eventually creates nonlinear response which gives changing center frequency versus amplitude. By measuring change of frequency versus amplitude, the nonlinear characteristics of the pipe and drivers can be compensated. Additional nonlinear behavior of the system due to adding liquid can then be determined relative to the response of calibration liquids such as water. The calibration liquids should be single phase with density comparable to the liquids to be characterized. This calibration procedure is useful for characterizing two phase liquids which have a nonlinear modulus and may be useful for identifying small percentages of gas in liquid.

Monitoring multiple resonant modes as described above can help reduce the effects of resonances from mechanical noises. Mechanical noises will be out of synchronization with the sweep rate of the driver transducers and therefore have incoherent effects on the multiple resonant frequencies. A regression fit to multiple center frequencies statistically reduces effects of mechanical noise at resonance frequencies.

Processing Techniques

The foregoing gives a sample of the use of the present invention; however, an actual implementation takes the respective detected resonant frequencies, amplitudes and associated bandwidths (preferably the 3 dB bandwidth, or Q) and converts them to the desired parameters (e.g., density or any of the other characteristics previously mentioned). Two techniques for doing this will next be described, but it is contemplated that other techniques (including a combination of empirical and mathematical) can be used and remain within the scope of the present invention. The two techniques to be described here are the use of an empirical neural network and the use of explicit mathematical algorithms.

Empirical Technique

An equation for estimating density, for example, from the $i^{th}$ resonance frequency is:

$$\text{Density}_i = A_i/(\text{Frequency}_i)^2 + B_i$$

Figure 20:
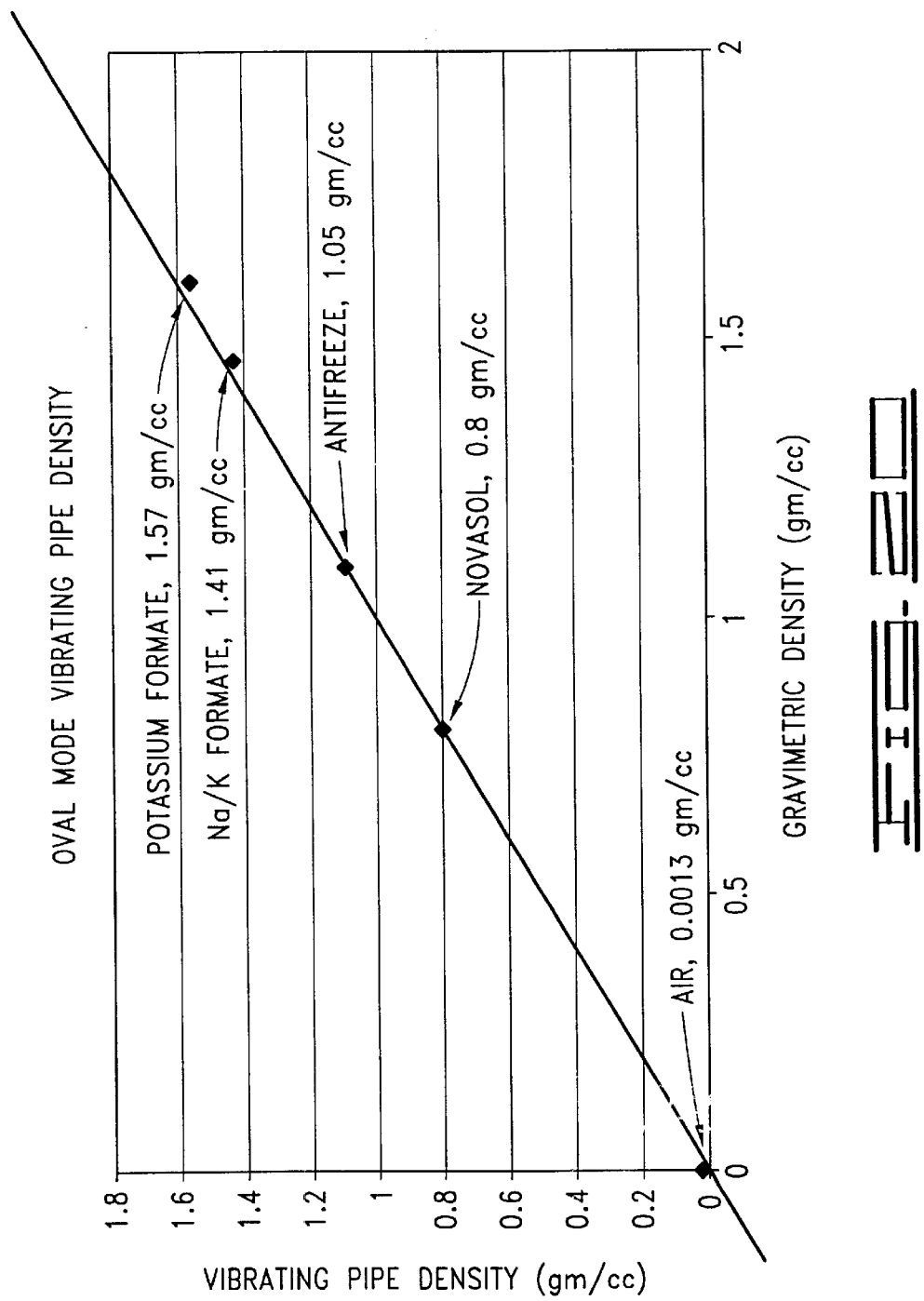
FIG. 20 shows the results from averaging calculated densities for each oval mode resonant frequency in tests using the identified fluids in a static state.

The preferred determination of the density is obtained by averaging the results for all relevant resonate frequencies for each respective mode (i.e., average of the above $A_i(\text{Frequency}_i)^2 + B_i$ for all the identified resonant frequencies for the respective mode), and averaging between or among two or more modes can be used if they relate to the same characteristics to be determined. For example, a flexural mode test can be performed to determine its correlation to a particular characteristic, density, for example. This is done with one or more known fluids, and from this the A and B values can be determined. The density for an unknown fluid can then be determined by using the A and B values with the resonant frequencies identified in a flexural mode test of the unknown fluid. An average is calculated using the individual values derived for each resonant frequency. The average can also include values derived from any other relevant mode; therefore, the present invention includes averaging within each mode (which alone may be used) and/or averaging using two or more modes. When multiple modes are used, the initial calculation for each mode is performed in the same manner as for the flexural mode mentioned above. FIG. 20 shows the results for averaging the calculated densities for each oval mode resonant frequency in a test using the identified fluids in a static state as described above. The vertical pipe test system was used on the fluids listed on the graph. The straight line manually fitted to the points is within ±0.015 gm/cc (gram per cubic centimeter) of the measured data points.

The values for the $A_i$'s and $B_i$'s of the above equation can be obtained by using calibration fluids with known densities and measured resonant frequencies for each mode of interest (flexural, hoop, oval, torsional). These values of calibration constants are then used to calculate the relevant characteristics of unknown fluids. The $A_i$'s and $B_i$'s are different functions of compressibility and viscosity. They are determined using fluids having known densities, compressibilities, and viscosities. Center frequencies and Q's responsive to the multiple frequency vibrations applied to the fluid test system are determined. The frequencies and Q's are dependent data input for a neural network computer. The independent data are the fluid densities, compressabilities, and viscosities for the calibration fluids. During a calibration run the neural network establishes predictive relations. From the predictive relations, the programmed computer then calculates density and other parameters for unknown fluids to which multiple frequency vibrations are applied in the test system.

Mathematical Technique

The following describes a mathematical approach in correlating detected response to actual parameter. Initially it is noted that frequency response (magnitude) curves are multi-modal about each resonance, that is, several relative maxima appear. Center frequency selection (absolute maxima) is complicated by presence of relative maxima. Described below is a technique to locate absolute maxima for any resonant frequency band, leading to proper center frequency identification. This methodology is then adapted to bandwidth limit identification.

Center Frequency Identification

Figure 24:
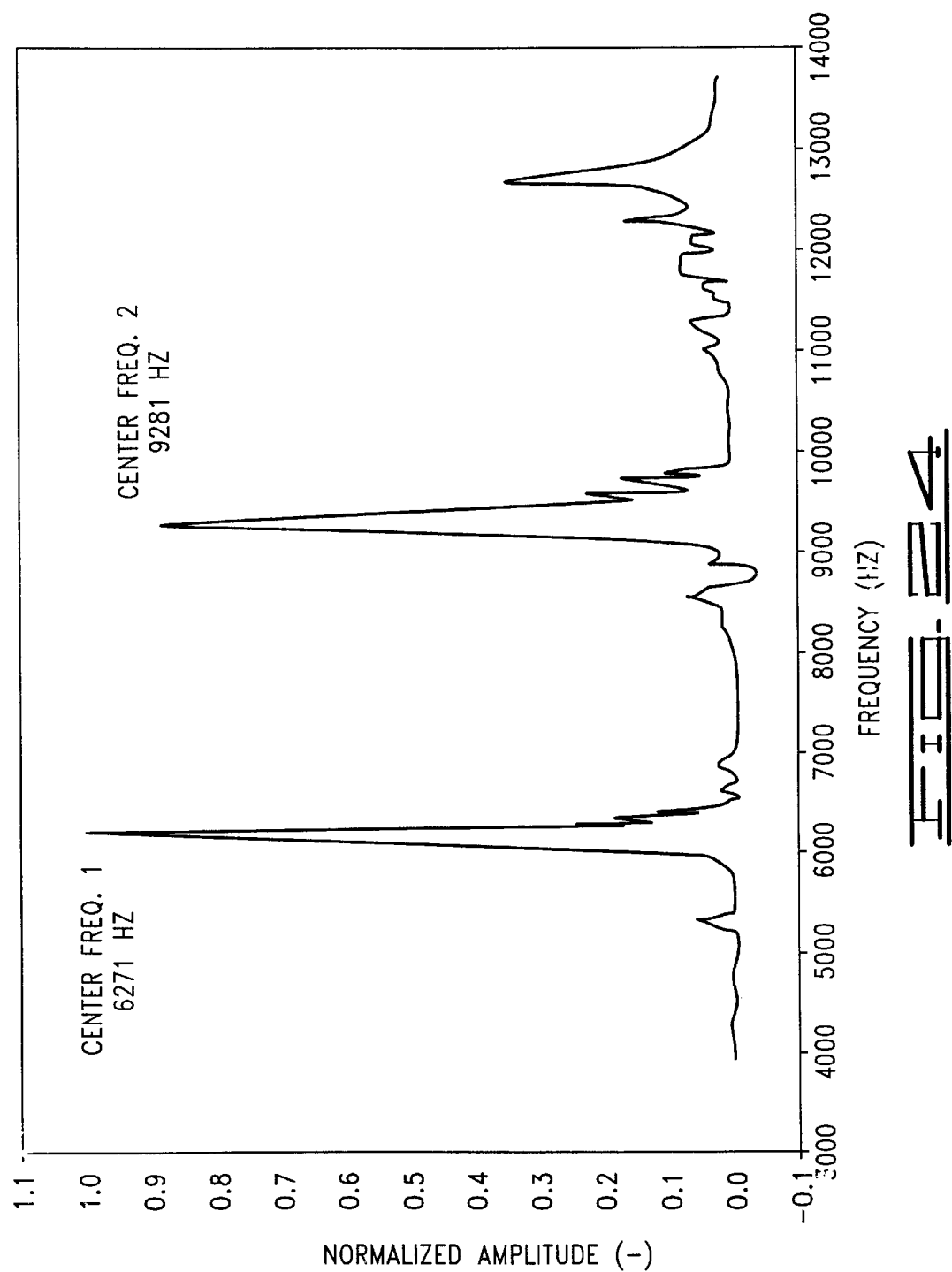
FIG. 24 shows a frequency domain data acquisition example for normalized densitometer response over a broad frequency range used to describe a mathematical analytical technique in the signal processing of one implementation of the present invention.
Figure 25:
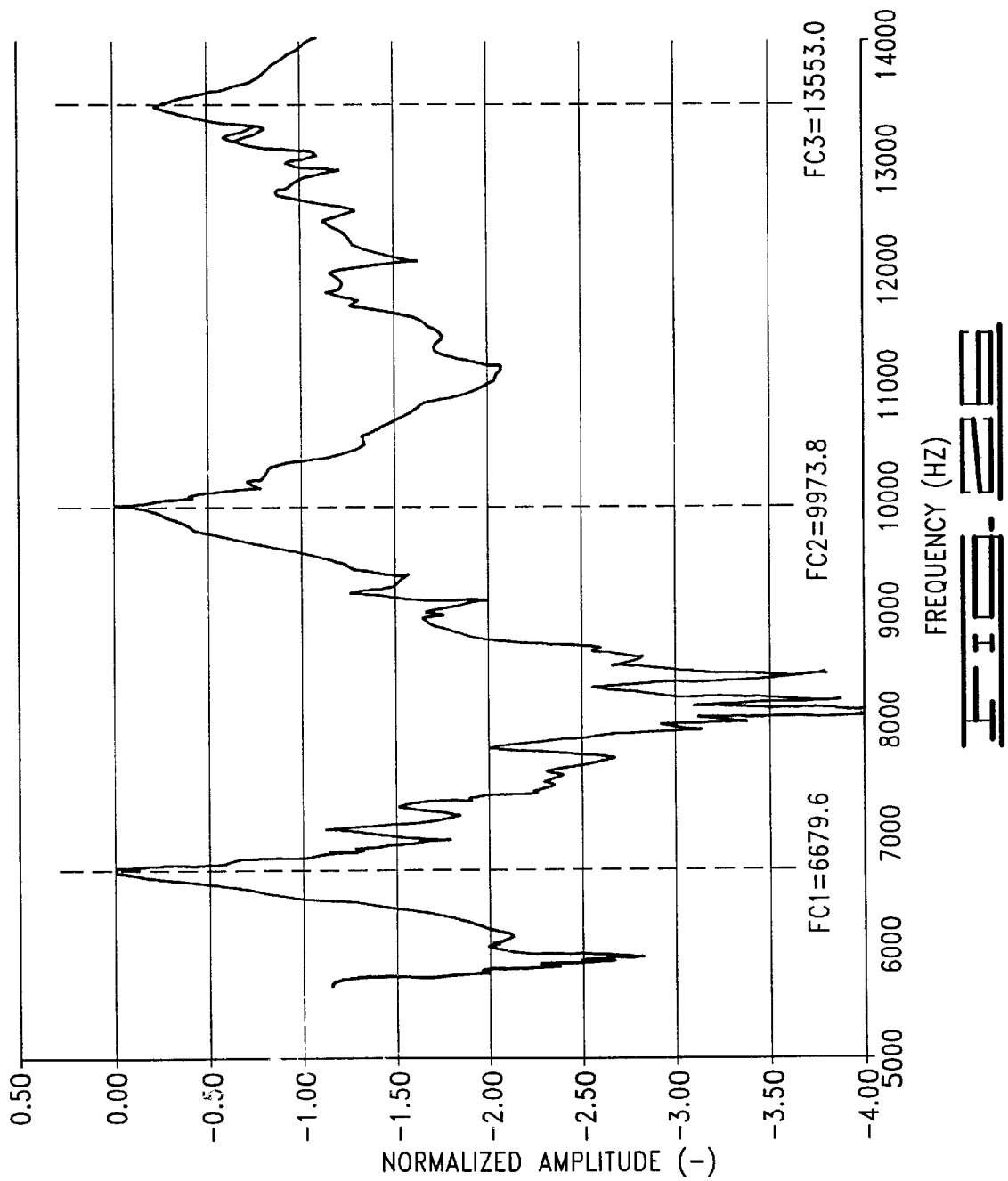

FIG. 24 provides a frequency domain data acquisition example that shows normalized densitometer response over a broad frequency range. Integrated receiver response can be somewhat noisy with multi-modal peaks. The challenge is to scan data, properly pick the absolute peak, then identify the corresponding resonant frequency. With multi-mode data, misidentification of the absolute maximum peak must be avoided.

Figure 25:
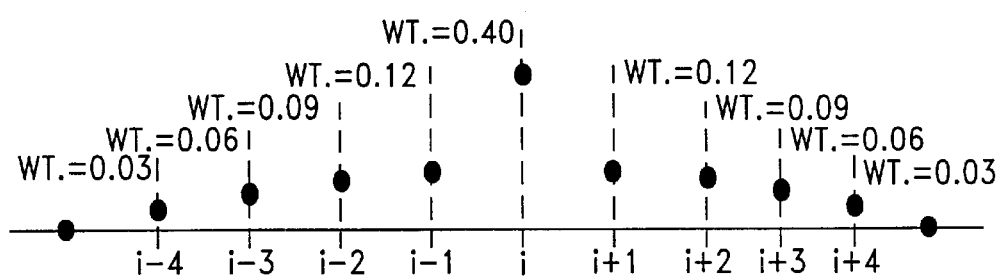
FIG. 25 shows a definition for a nine point moving average used in the mathematical analytical technique to smooth received resonant signals.

Some smoothing is initially used to condition all piezo-electric receiver data. In one test, a nine point moving average (defined in FIG. 25) was used. All nine weights ($Wt_i$) add to unity (1.0). Multi-mode traces still existed after smoothing, but some point-to-point noisiness was reduced. A Fibonacci search method was then used to locate peak amplitudes.

FIG. 26 provides a densitometer frequency response plot with multi-layer Fibonacci searches employed. All three peak amplitudes were properly identified, leading to proper center frequency identification.

Bandwidth Identification

Many of the problems associated with center frequency identification also apply to bandwidth identification. Detection of upper and lower bandwidth frequency limits $f_U$ and $f_L$ is useful for interpreting energy dissipation of the fluid, which relates to viscosity.

Referring to FIG. 27, assume that center frequency $f_C = f$[ifc] with index 'ifc' having been identified. The half-power amplitude lies at approximately −0.3 on a log-normalized scale. Lower bandwidth limit index 'ifl' can be readily identified, from which $f_L = f[ifl]$ is achieved. Note, however, that several crossings of the −0.3 threshold can occur when noisy data exists. In this case, the best solution is to identify all −0.3 crossings so that an overall, 'average' bandwidth limit frequency can be determined.

A modified Fibonacci-type search can be applied. The center frequency index ifc can be used as the reference point. Lower bandwidth limit data index 'ifl' can be identified by searching data to the left (lower indices) and upper bandwidth limit data index 'ifu' can be identified by searching data to the right (upper indices). When searching each peak for bandwidth limits, the log-normalized amplitude must be considered. The data set must be either re-normalized or bandwidth limits must be adjusted.

Conversion of Frequency to Density

Frequency uncertainty $\Delta f_n$ arises from two sources. One uncertainty source is born from signal discretization that is unavoidable. The other source relates to center frequency selection, but this source of uncertainty can be avoided or reduced by using the mathematical technique referred to above. Once output frequencies have been determined, however, they can be converted to measurements of the respective characteristics using the formula and neural network approach referred to above. In general, however, each identified resonant frequency is correlated to the respective characteristic and an average of all the values is calculated to define the characteristic measurement that is to be output or otherwise used. This is performed within each excitation mode and across all respective modes used as desired.

Accordingly, one aspect of the present invention provides a method of monitoring a fluid comprising: imparting mechanical waves into a fluid to be monitored, wherein the mechanical waves have frequencies within a predetermined range; generating alternating current electric signals in response to transmission characteristics of the fluid relative to the imparted mechanical waves; and indicating a characteristic of the fluid in response at least to identified frequencies within the alternating current electric signals. In the preferred embodiments described above, the identified frequencies are resonant frequencies of a system which includes the fluid. A particular implementation of the method more specifically comprises: flowing a fluid through a conduit; driving at least one of one or more transducers disposed adjacent the conduit to impart energy to the conduit to deform the conduit in a flexural mode; driving at least one of the one or more transducers to impart energy to the conduit to deform the conduit in a radial hoop mode; driving at least one of the one or more transducers to impart energy to the conduit to deform the conduit in a radial oval mode; and generating signals, with at least one of the one or more transducers, in response to the driving steps. This can further comprise indicating at least one characteristic of the flowing fluid in response to the generated signals.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. A method of monitoring a fluid, comprising:
   imparting multiple frequency vibration-inducing energy to a system including a conduit and fluid; and
   sensing frequency signals from the system responsive to at least part of the imparted multiple frequency vibration-inducing energy and identifying a plurality of distinguishing frequencies within the sensed frequencies and measuring a characteristic of the fluid in response to the identified plurality of distinguishing frequencies, wherein the characteristic is in the group consisting of density, compressibility and viscosity.

2. A method as defined in claim 1, wherein measuring a characteristic includes using an averaging calculation with the distinguishing frequencies identified from the sensed frequency signals.

3. A method as defined in claim 1, wherein imparting multiple frequency vibration-inducing energy includes driving the system at multiple frequencies in multiple modes.

4. A method of monitoring a fluid as defined in claim 1, wherein:
   the method further comprises flowing the fluid through the conduit;
   imparting multiple frequency vibration-inducing energy includes:
      driving at least one of one or more transducers disposed adjacent the conduit to impart energy to the conduit to deform the conduit in a flexural mode;
      driving at least one of the one or more transducers to impart energy to the conduit to deform the conduit in a radial hoop mode; and
      driving at least one of the one or more transducers to impart energy to the conduit to deform the conduit in a radial oval mode; and
   sensing frequency signals includes generating signals, with at least one of the one or more transducers, in response to the driving steps.

5. A method as defined in claim 4, wherein:
   identifying a plurality of distinguishing frequencies includes identifying resonant frequencies in the generated signals for each mode; and
   measuring a characteristic of the fluid occurs in response to an averaging calculation using the identified resonant frequencies.

6. A method as defined in claim 1, wherein imparting multiple frequency vibration-inducing energy includes using a plurality of inertial transducers connected to the conduit.

7. A method as defined in claim 1, wherein imparting multiple frequency vibration-inducing energy includes operating a plurality of transducers mechanically mounted only to the conduit.

8. A method as defined in claim 2, wherein measuring a characteristic further includes using calibration information from a respective plurality of resonant frequency responses for each of a plurality of calibration fluids.

9. A method as defined in claim 8, wherein imparting multiple frequency vibration-inducing energy includes driving the system at multiple frequencies in multiple modes.

10. A fluid property monitor, comprising:
    a transducer assembly to impart multiple frequency energy to a conduit in multiple modes, and to receive resonant frequency energy from the conduit, wherein the resonant frequency energy is responsive to the imparted energy, the conduit and a fluid in the conduit;
    a frequency signal generator connected to cause respective multiple frequency energy to be transferred through the transducer assembly to the conduit for each of the multiple modes; and
    a spectral analysis signal processor connected to receive and process electrical signals generated in response to vibrations propagated through the conduit and the fluid in the conduit in response to transferred multiple frequency energy so that multiple distinguishing resonant frequencies are identified for each mode for determining a respective characteristic of the fluid.

11. A fluid property monitor as defined in claim 10, wherein the multiple frequency energy is acoustic energy within the range of about 100 hertz to about 20,000 hertz.

12. A fluid property monitor as defined in claim 10, wherein the transducer assembly mechanically mounts only to the conduit.

13. A fluid property monitor as defined in claim 10, wherein the transducer assembly includes a transducer comprising a base held adjacent the conduit and having stacked thereon:
    a first insulating washer adjacent the base;
    a first electrode adjacent the first insulating washer;
    a piezoelectric member adjacent the first electrode;
    a second electrode adjacent the piezoelectric member;
    a second insulating washer adjacent the second electrode; and
    a Bellville spring washer adjacent the second insulating washer.

14. A fluid property monitor as defined in claim 10, wherein the transducer assembly includes:
    a moment arm member connected to and extending radially from the conduit; and
    a vibration-inducing member connected to the moment arm member at a location thereon spaced from the conduit such that vibrations generated by the vibration-inducing member are applied to the conduit through the moment arm member.

15. A fluid property monitor to measure a respective characteristic of a fluid in the group consisting of a cement slurry, a stimulation fluid, and a drilling mud, comprising a transducer assembly configured to mount on the outside of a conduit, which conduit has the fluid under pressure, for imparting multiple frequency energy to the conduit so that the conduit deforms in multiple modes of vibration of cylindrical shells including at least flexural and oval modes of standing wave patterns, and for receiving resonant frequency energy from the conduit, wherein the resonant frequency energy is at a plurality of frequencies responsive to the imparted energy, the conduit and the respective characteristic of the fluid in the conduit.

16. A fluid property monitor as defined in claim 15, wherein the multiple frequency energy is acoustic energy having frequencies within the range of about 100 hertz to about 20,000 hertz.

17. A fluid property monitor as defined in claim 15, wherein the multiple frequency energy is acoustic energy having frequencies within the range of about 3,000 hertz to about 14,000 hertz.

18. A fluid property monitor as defined in claim 15, wherein the respective characteristic is in the group consisting of density, compressibility, and viscosity.

19. A fluid property monitor as defined in claim 15, wherein the transducer assembly includes a transducer comprising a base held adjacent the conduit and having stacked thereon:
 a first insulating washer adjacent the base;
 a first electrode adjacent the first insulating washer,
 a piezoelectric member adjacent the first electrode;
 a second electrode adjacent the piezoelectric member;
 a second insulating washer adjacent the second electrode; and
 a Bellville spring washer adjacent the second insulating washer.

20. A fluid property monitor as defined in claim 15, wherein the transducer assembly includes:
 a moment arm member connected to and extending radially from the conduit; and
 a vibration-inducing member connected to the moment arm member at a location thereon spaced from the conduit such that vibrations generated by the vibration-inducing member are applied to the conduit through the moment arm member.

21. A method of measuring a characteristic of a fluid, comprising:
 imparting multiple frequency energy at frequencies within the range of about 100 hertz to about 20,000 hertz to a conduit and fluid system such that the conduit is deformed to vibrate in at least a flexural mode and an oval mode;
 sensing a plurality of frequency signals from the conduit and fluid system responsive to at least part of the imparted multiple frequency energy; and
 determining a respective characteristic of the conduit and fluid system in response to the sensed plurality of frequency signals.

22. A method of monitoring a fluid as defined in claim 21, wherein the multiple frequency energy is acoustic energy having frequencies within the range of about 3,000 hertz to about 14,000 hertz.

23. A method of monitoring a fluid as defined in claim 22, wherein the at least one characteristic is in the group consisting of density, compressibility, and viscosity.

24. A method of monitoring a fluid as defined in claim 21, wherein the at least one characteristic is in the group consisting of density, compressibility, and viscosity.

25. A method of monitoring a fluid as defined in claim 21, wherein determining at least one characteristic of the conduit and fluid system includes using resonant frequencies and associated bandwidths from the sensed plurality of frequency signals.

26. A method as defined in claim 21, wherein determining a respective characteristic includes using calibration information from a respective plurality of resonant frequency responses for each of a plurality of calibration fluids and using an average of the sensed plurality of frequency signals.

27. A method of measuring density of a fluid, comprising:
 imparting to a system, for each of at least three vibrational modes, respective multiple frequency energy at frequencies within the range of about 100 hertz to about 20,000 hertz such that the conduit is deformed to vibrate, wherein the system includes a conduit having a fluid whose density is to be measured and wherein the fluid is in the group consisting of a cement slurry, a stimulation fluid and a drilling mud;
 sensing a plurality of distinguishing resonant frequency signals from the system responsive to at least part of the imparted multiple frequency energy; and
 measuring density of the fluid in response to the sensed plurality of frequency signals, including using calibration information from a respective plurality of resonant frequency responses for each of a plurality of calibration fluids and using an averaging calculation with the plurality of distinguishing resonant frequency signals.

* * * * *